(12) United States Patent
Choi et al.

(10) Patent No.: US 10,299,690 B2
(45) Date of Patent: May 28, 2019

(54) ELECTRONIC DEVICE AND METHOD FOR MEASURING BIOMETRIC INFORMATION

(71) Applicant: Samsung Electronics Co., Ltd., Suwon-si, Gyeonggi-do (KR)

(72) Inventors: Ah-Young Choi, Seoul (KR); Young-Hyun Kim, Suwon-si (KR); Seong-Wook Jo, Suwon-si (KR); Jin-Hong Min, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 362 days.

(21) Appl. No.: 15/044,442

(22) Filed: Feb. 16, 2016

(65) Prior Publication Data

US 2016/0235341 A1 Aug. 18, 2016

(30) Foreign Application Priority Data

Feb. 16, 2015 (KR) .......................... 10-2015-0023713

(51) Int. Cl.
| | |
|---|---|
| *A61B 5/0408* | (2006.01) |
| *A61B 5/00* | (2006.01) |
| *A61B 5/024* | (2006.01) |
| *A61B 5/0478* | (2006.01) |
| *A61B 5/0496* | (2006.01) |
| *A61B 5/0488* | (2006.01) |
| *A61B 5/0492* | (2006.01) |

(Continued)

(52) U.S. Cl.
CPC .......... *A61B 5/04085* (2013.01); *A61B 5/024* (2013.01); *A61B 5/6898* (2013.01); *A61B 5/01* (2013.01); *A61B 5/021* (2013.01); *A61B 5/0478* (2013.01); *A61B 5/0488* (2013.01); *A61B 5/0492* (2013.01); *A61B 5/0496* (2013.01); *A61B 5/04884* (2013.01); *A61B 5/14532* (2013.01); *A61B 5/165* (2013.01); *A61B 5/4035* (2013.01); *A61B 2562/0219* (2013.01)

(58) Field of Classification Search
USPC .................................................. 600/300–301
See application file for complete search history.

(56) References Cited

U.S. PATENT DOCUMENTS

| | | |
|---|---|---|
| 6,526,315 B1 | 2/2003 | Inagawa et al. |
| 6,718,200 B2 | 4/2004 | Marmaropoulos et al. |

(Continued)

FOREIGN PATENT DOCUMENTS

| | | |
|---|---|---|
| EP | 0545014 A1 | 6/1993 |
| EP | 1138259 A2 | 10/2001 |

(Continued)

*Primary Examiner* — Nicole F Lavert
(74) *Attorney, Agent, or Firm* — Jefferson IP Law, LLP

(57) ABSTRACT

An electronic device for measuring biometric information is provided. The electronic device includes a sensor unit configured to detect an attitude of the electronic device, a biometric information measurement unit configured to detect biometric information on an examinee through a plurality of electrodes formed on at least one surface of the electronic device, a switch unit including a plurality of switches electrically connected to the plurality of electrodes and a controller configured to recognize an array of the plurality of electrodes based on the detected attitude of the electronic device and control the switch unit such that the recognized electrode array corresponds to a preset electrode array.

20 Claims, 30 Drawing Sheets

(51) Int. Cl.
    *A61B 5/01*         (2006.01)
    *A61B 5/021*       (2006.01)
    *A61B 5/145*       (2006.01)
    *A61B 5/16*         (2006.01)

(56) References Cited

U.S. PATENT DOCUMENTS

| | | |
|---|---|---|
| 7,698,830 B2 | 4/2010 | Townsend et al. |
| 2008/0208028 A1 | 8/2008 | Thijs et al. |
| 2010/0113961 A1 | 5/2010 | Ohlander et al. |
| 2011/0152695 A1* | 6/2011 | Granqvist ............ A61B 5/0006 |
| | | 600/481 |
| 2012/0130645 A1 | 5/2012 | Garudadri et al. |
| 2014/0106816 A1 | 4/2014 | Shimuta |
| 2014/0358012 A1* | 12/2014 | Richards ............ A61B 5/02438 |
| | | 600/479 |

FOREIGN PATENT DOCUMENTS

| | | |
|---|---|---|
| JP | 2008-536605 A | 9/2008 |
| JP | 2008-229092 A | 10/2008 |
| JP | 2009-111928 A | 5/2009 |
| JP | 2014-238696 A | 12/2014 |
| KR | 20-0361688 Y1 | 9/2004 |
| KR | 10-2007-0083334 A | 8/2007 |
| KR | 10-2009-0004249 A | 1/2009 |
| KR | 10-2011-0119475 A | 11/2011 |
| KR | 10-2013-0027187 A | 3/2013 |
| KR | 10-2013-0027413 A | 3/2013 |
| WO | 2011/075767 A1 | 6/2011 |

\* cited by examiner

ELECTRONIC DEVICE AND METHOD FOR MEASURING BIOMETRIC INFORMATION

CROSS-REFERENCE TO RELATED APPLICATION(S)

This application claims the benefit under 35 U.S.C. § 119(a) of a Korean patent application filed on Feb. 16, 2015 in the Korean Intellectual Property Office and assigned Serial number 10-2015-0023713, the entire disclosure of which is hereby incorporated by reference.

TECHNICAL FIELD

The present disclosure relates to an electronic device and a method of measuring biometric information. More particularly, the present disclosure relates to an electronic device and a method capable of measuring accurate biometric information regardless of an electrode array of electrodes.

BACKGROUND

Recently, as interest in health increases, many people carry a device to measure and immediately identify their own biometric information, thereby increasing demands for management of their own health. According to the demands, a portable biometric information measuring device by which the user can determine his/her own health at anytime and anywhere is spotlighted. To this end, the biometric information measuring device may be included in the form of a module in an electronic device, such as a portable terminal, which can be easily carried and conveniently used, or may be provided in the form of an application to be downloaded.

Such an electronic device for measuring biometric information can measure biometric information by attaching a plurality of electrodes to a corresponding part of the body or bringing the plurality of electrodes into contact with the corresponding part of the body according to the type of biometric information, analyze the measured biometric information, and immediately identify a health state through various provided biometric indexes and a body composition of the examinee. Accordingly, the examinee can determine his/her current health state through the provided biometric indexes and body composition and thus easily determine a checkup list which requires exercise, diet, rehabilitation treatment, or a complete medical examination according to the health state.

However, an electronic device for measuring biometric information of the related art has determined locations, directions, polarities, and electrode channel arrangements of a plurality of electrodes according to biometric information to be measured. Accordingly, in order to measure biometric information, a user or an examinee should grasp the locations, directions, polarities, and electrode channel arrangements of the plurality of electrodes and accurately place the electronic device on a body part required by each electrode.

If the electronic device is not placed on the required body part according to the locations, directions, polarities, and electrode channel arrangements of the plurality of electrodes, accurate biometric information cannot be measured and a biometric index and body composition analyzed based on the measured biometric information are not reliable. Further, in some cases, the measurement of biometric information may not be performed at all. Accordingly, the examinee or the user has to recognize in advance the locations, directions, polarities, and electrode channel arrangements of the plurality of electrodes to measure the accurate biometric information, so that the examinee or the user may feel difficulty, cumbersomeness, and inconvenience in measuring biometric information.

Therefore, a need exists for an electronic device and a method for measuring biometric information, which can acquire accurate biometric information regardless of an electrode array including locations, directions, polarities, and electrode channel arrangements of a plurality of electrodes.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide an electronic device and a method for measuring biometric information, which can acquire accurate biometric information regardless of an electrode array including locations, directions, polarities, and electrode channel arrangements of a plurality of electrodes.

In accordance with an aspect of the present disclosure, an electronic device for measuring biometric information is provided. The electronic device includes a complex location sensor unit configured to detect a plurality of pieces of location information in a measurement point, a biometric information measurement unit configured to detect biometric information through a plurality of electrodes formed on at least one surface of the electronic device, a switch unit electrically connected to the biometric information measurement unit and including a plurality of switches corresponding to the plurality of electrodes, respectively, and a controller configured to recognize an electrode array of the plurality of electrodes according to an attitude of the electronic device in the measurement point based on the plurality of pieces of detected location information and control the switch unit such that the recognized electrode array corresponds to a preset electrode array.

In accordance with another aspect of the present disclosure, a method of measuring biometric information by an electronic device is provided. The method includes detecting a plurality of pieces of location information in a measurement point, recognizing an electrode array of a plurality of electrodes formed at least one surface of the electronic device according to an attitude of the electronic device in the measurement point based on the plurality of pieces of detected location information, determining whether the recognized electrode array is changed by comparing the recognized electrode array and a preset electrode array, controlling a switch unit including a plurality of switches corresponding to the plurality of electrodes, respectively, such that the recognized electrode array corresponds to the preset electrode array and is connected to a biometric information measurement unit based on a result of the determination, and analyzing health state information of an examinee by detecting biometric information by the biometric information measurement unit through the plurality of electrodes.

In accordance with another aspect of the present disclosure, an electronic device for measuring biometric information is provided. The electronic device includes a complex location sensor unit configured to detect a plurality of pieces of location information in a measurement point, an auxiliary sensor unit configured to detect a plurality of pieces of auxiliary detection information in the measurement point, a biometric information measurement unit configured to detect biometric information through a plurality of electrodes formed on at least one surface of the electronic device, a switch unit electrically connected to the biometric information measurement unit and including a plurality of switches (or one switch including at least one input port and at least one output port) corresponding to the plurality of electrodes, respectively, and a controller configured to determine a measurement pose of the examinee according to an attitude of the electronic device based on the plurality of pieces of detected location information and the plurality of pieces of detected auxiliary detection information and control the switch unit to change an electrode array of the plurality of electrodes into an electrode array corresponding to the determined measurement pose among preset measurement pose-specific electrode arrays.

In accordance with another aspect of the present disclosure, a method of measuring biometric information by an electronic device is provided. The method includes detecting a plurality of pieces of location information and a plurality of pieces of auxiliary detection information in a measurement point, determining a measurement pose of an examinee according to an attitude of the electronic device in the measurement point based on the plurality of pieces of detected location information and the plurality of pieces of auxiliary detection information, controlling a switch unit including a plurality of switches corresponding to the plurality of electrodes, respectively, such that an electrode array of a plurality of electrodes formed on at least one surface of the electronic device corresponds to a preset electrode array corresponding to the determined measurement pose among preset measurement pose-specific electrode arrays and is connected to a biometric information measurement unit and analyzing health state information on the examinee based on the biometric information detected by the biometric information measurement unit through the plurality of electrodes.

According to various embodiments of the present disclosure, it is possible to improve user convenience by measuring biometric information after changing an electrode array according to locations and attitudes of a plurality of electrodes automatically recognized in a measurement point without a need to recognize in advance the electrode array including a location, a direction, a polarity, and an electrode channel arrangement of each of the plurality of electrodes when biometric information is measured.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
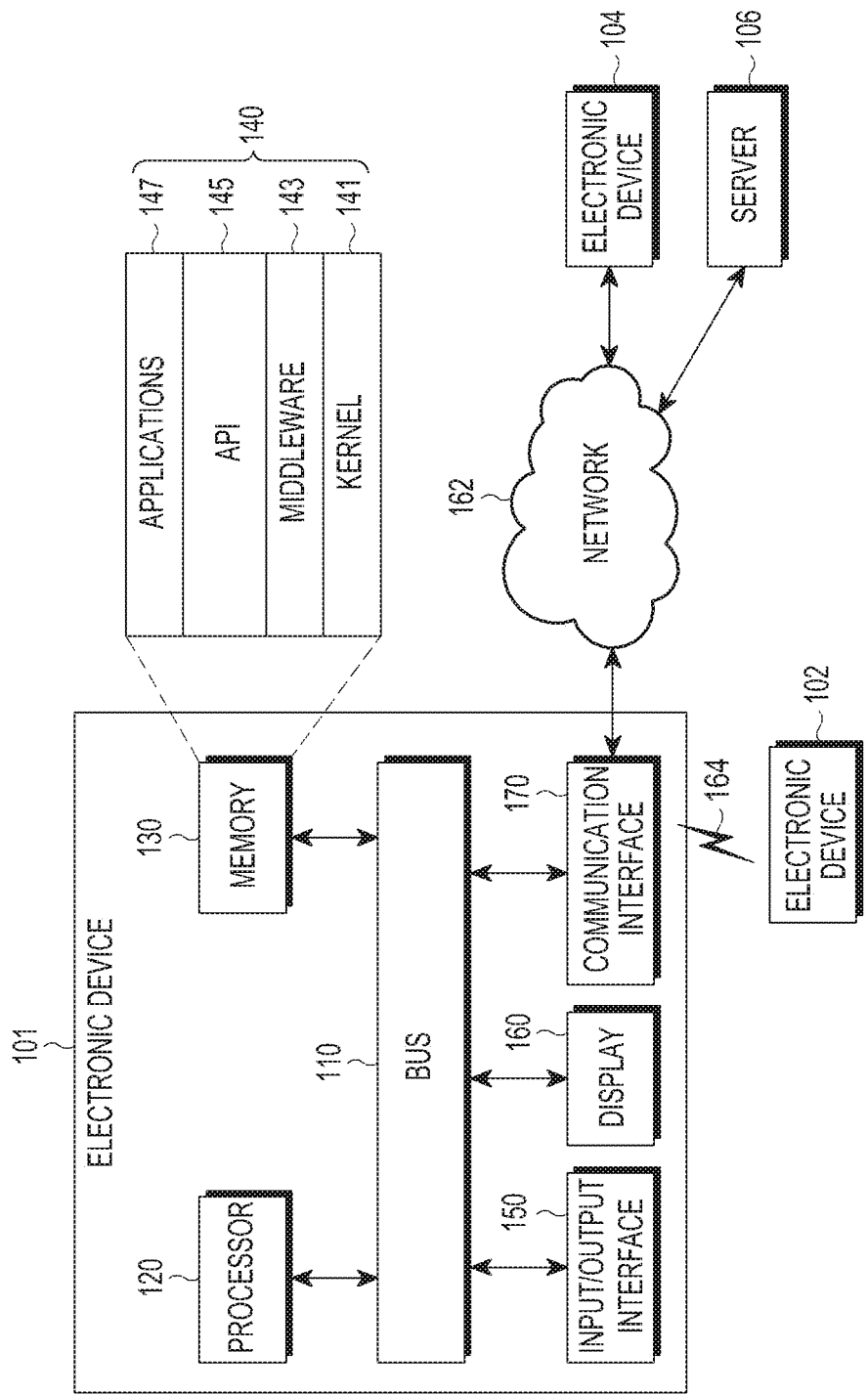
FIG. 1 illustrates an electronic device within a network environment according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

In embodiments of the present disclosure, the expression "have", "may have", "include" or "may include" refers to existence of a corresponding feature (for example, a numerical value, a function, an operation, or components, such as elements), and does not exclude existence of additional features.

In embodiments of the present disclosure, the expression "A or B", "at least one of A or/and B", or "one or more of A or/and B" may include all possible combinations of the items listed. For example, the expression "A or B", "at least one of A and B", or "at least one of A or B" may include (1) at least one A, (2) at least one B, or (3) both at least one A and at least one B.

The expressions, such as "first", "second", and the like, used in various embodiments of the present disclosure may modify various elements regardless of order or importance, and do not limit corresponding elements. The above expressions are used merely for the purpose of distinguishing an element from the other elements. For example, a first user device and a second user device indicate different user devices although both of them are user devices. For example, a first element may be termed a second element, and similarly, a second element may be termed a first element without departing from the scope of the present disclosure.

It should be understood that when an element (for example, a first element) is referred to as being (operatively or communicatively) "connected," or "coupled," to another element (for example, a second element), it may be directly connected or coupled directly to the other element or any other element (for example, a third element) may be interposer between them. In contrast, it may be understood that when an element (for example, a first element) is referred to as being "directly connected," or "directly coupled" to another element (i.e., the second element), there are no element (for example, the third element) interposed between them.

As used herein, the expression "configured to" may be interchangeably used with the expression "suitable for", "having the capability to", "designed to", "adapted to", "made to", or "capable of". The expression "configured to" may not necessarily mean "specially designed to" in terms of hardware. Alternatively, in some situations, the expression "device configured to" may mean that the device, together with other devices or components, "is able to". For example, the phrase "processor adapted (or configured) to perform A, B, and C" may mean a dedicated processor (for example, an embedded processor) only for performing the corresponding operations or a generic-purpose processor (for example, a central processing unit (CPU) or an application processor (AP)) that can perform the corresponding operations by executing one or more software programs stored in a memory device.

Terms used in this specification are merely used to describe a specific embodiment and may not be intended to limit the scope of another element. As used herein, singular forms may include plural forms as well unless the context clearly indicates otherwise. Unless defined otherwise, all terms used herein, including technical terms and scientific terms, may have the same meaning as commonly understood by a person of ordinary skill in the art to which the present disclosure pertains. Terms, such as those defined in commonly used dictionaries, should be interpreted as having a meaning that is the same or similar to their meaning in the context of the relevant art and will not be interpreted in an idealized or overly formal sense unless expressly so defined herein. In some cases, even the term defined in embodiments of the present disclosure should not be interpreted to exclude embodiments of the present disclosure.

For example, the electronic device may include at least one of a smartphone, a tablet personal computer (PC), a mobile phone, a video phone, an electronic book (e-book) reader, a desktop PC, a laptop PC, a netbook computer, a personal digital assistant (PDA), a portable multimedia player (PMP), a moving picture experts group phase 1 or phase 2 (MPEG-1 or MPEG-2) audio layer 3 (MP3) player, a mobile medical appliance, a camera, and a wearable device (for example, a head-mounted-device (HMD), such as electronic glasses, electronic clothes, an electronic bracelet, an electronic necklace, an electronic appcessory, electronic tattoos, a smart watch, and the like).

In various embodiments of the present disclosure, an electronic device may be a smart home appliance. The home appliance may include at least one of, for example, a television (TV), a digital video disc (DVD) player, an audio, a refrigerator, an air conditioner, a vacuum cleaner, an oven, a microwave oven, a washing machine, an air cleaner, a set-top box, a home automation control panel, a security control panel, a TV box (for example, Samsung HomeSync™, Apple TV™, or Google TV™), a game console (for example, Xbox™ and PlayStation™), an electronic dictionary, an electronic key, a camcorder, and an electronic photo frame.

According to another embodiment of the present disclosure, the electronic device may include at least one of various medical devices (for example, various portable medical measuring devices (i.e., a blood glucose monitoring device, a heart rate monitoring device, a blood pressure measuring device, a body temperature measuring device, and the like), a magnetic resonance angiography (MRA), a magnetic resonance imaging (MRI), a computed tomography (CT) machine, and an ultrasonic machine), a navigation device, a global positioning system (GPS) receiver, an event data recorder (EDR), a flight data recorder (FDR), a vehicle infotainment devices, an electronic devices for a ship (for example, a navigation device for a ship, and a gyro-compass), avionics, security devices, an automotive head unit, a robot for home or industry, an automatic teller's machine (ATM) in banks, point of sales (POS) in a shop, or internet device of things (for example, a light bulb, various sensors, an electric or gas meter, a sprinkler device, a fire alarm, a thermostat, a streetlamp, a toaster, a sporting goods, a hot water tank, a heater, a boiler, and the like).

According to various embodiments of the present disclosure, the electronic device may include at least one of a part of furniture or a building/structure, an electronic board, an electronic signature receiving device, a projector, and various kinds of measuring instruments (for example, a water meter, an electric meter, a gas meter, and a radio wave meter). In various embodiments of the present disclosure, an electronic device may be a combination of one or more of the aforementioned various devices. An electronic device, according to an embodiment of the present disclosure, may be a flexible electronic device. Further, an electronic device, according to an embodiment of the present disclosure, is not limited to the aforementioned devices and may include a new electronic device according to technological advance.

Hereinafter, electronic devices, according to various embodiments of the present disclosure, will be described with reference to the accompanying drawings. As used herein, the term "user" may indicate a person who uses an electronic device or a device (for example, an artificial intelligence electronic device) that uses an electronic device.

FIG. 1 illustrates an electronic device within a network environment according to various embodiments of the present disclosure.

Referring to FIG. 1, an electronic device 101 may include a bus 110, a processor 120, a memory 130, an input/output interface 150, a display 160, and a communication interface 170. According to various embodiments of the present disclosure, the electronic device 101 may omit at least one of the elements or further include other elements.

The bus 110 may include, for example, a circuit that interconnects the elements 110 to 170 and transfers communication (for example, a control message and/or data) between the elements.

The processor 120 may include one or more of a CPU, an AP, and a communication processor (CP). The processor 120 may perform, for example, an operation or data processing on control and/or communication of at least one other element of the electronic device 101.

The memory 130 may include a volatile memory and/or a non-volatile memory. The memory 130 may store, for example, commands or data relating to at least one other element of the electronic device 101. According to an embodiment of the present disclosure, the memory 130 may store software and/or a program 140. The program 140 may include, for example, a kernel 141, middleware 143, an application programming interface (API) 145, and/or application programs (or "applications") 147. At least some of the kernel 141, the middleware 143, and the API 145 may be referred to as an operating system (OS).

The kernel 141 may control or manage system resources (for example, the bus 110, the processor 120, or the memory 130) used to execute an operation or function implemented in other programs (for example, the middleware 143, the API 145, or the application programs 147). Furthermore, the kernel 141 may provide an interface by which the middleware 143, the API 145, or the application programs 147 may access the individual elements of the electronic device 101 to control or manage system resources.

The middleware 143 may serve as, for example, an intermediary that allows the API 145 or the application programs 147 to communicate with the kernel 141 to transmit/receive data. Furthermore, in regard to task requests received from the application programs 147, the middleware 143 may perform a control (for example, scheduling or load balancing) on the task requests using, for example, a method of assigning a priority for using the system resources (for example, the bus 110, the processor 120, or the memory 130) of the electronic device 101 to at least one of the application programs 147.

The API 145 is, for example, an interface by which the applications 147 control functions provided from the kernel 141 or the middleware 143, and may include, for example, at least one interface or function (for example, command) for file control, window control, image processing, or text control.

The input/output interface 150 may serve as, for example, an interface that can transfer commands or data input from a user or another external device to the other element(s) of the electronic device 101. Furthermore, the input/output interface 150 may output commands or data received from the other element(s) of the electronic device 101 to the user or the other external device.

The display 160 may include, for example, a liquid crystal display (LCD), a light emitting diode (LED) display, an organic LED (OLED) display, a micro electro mechanical system (MEMS) display, or an electronic paper display. The display 160 may display, for example, various types of content (for example, text, images, videos, icons, or symbols) to the user. The display 160 may include a touch screen, and may receive, for example, a touch input, a gesture input, a proximity input, or a hovering input using an electronic pen or the user's body part.

The communication interface 170 may configure, for example, communication between the electronic device 101 and an external device (for example, a first external electronic device 102, a second external electronic device 104, or a server 106). For example, the communication interface 170 may be connected to a network 162 through a wireless communication (i.e., a wireless communication 164) or a wired communication to communicate with the external device (for example, the second external electronic device 104 or the server 106).

The wireless communication may use, for example, at least one of long term evolution (LTE), LTE-advanced (LTE-A), code division multiple access (CDMA), wideband CDMA (WCDMA), universal mobile telecommunications system (UMTS), wireless broadband (WiBro), and global system for mobile communications (GSM), for example, as a cellular communication protocol. The wired communication may include, for example, at least one of a universal serial bus (USB), a high definition multimedia interface (HDMI), recommended standard 232 (RS-232), and a plain old telephone service (POTS). The network 162 may include a communication network, for example, at least one of a computer network (for example, a local area network (LAN) or a wide area network (WAN)), the Internet, and a telephone network.

Each of the first external electronic device 102 and the second external electronic device 104 may be a device which is the same as or different from the electronic device 101. According to an embodiment of the present disclosure, the server 106 may include a group of one or more servers. According to various embodiments of the present disclosure, all or some of the operations performed by the electronic device 101 may be performed by another electronic device or a plurality of electronic devices (for example, the first external electronic device 102, the second external electronic device 104, or the server 106). According to an embodiment of the present disclosure, when the electronic device 101 should perform some functions or services automatically or by a request, the electronic device 101 may make a request for performing at least some of the functions related to the functions or services to another device (for example, the first external electronic device 102, the second external electronic device 104, or the server 106) instead of performing the functions or services by itself. The other electronic device (for example, the first external electronic device 102, the second external electronic device 104, or the server 106) may carry out the requested functions or the additional functions and transfer the result, obtained by carrying out the functions, to the electronic device 101. The electronic device 101 may provide the requested functions or services by processing the received result as it is or additionally. To achieve this, for example, cloud computing, distributed computing, or client-server computing technology may be used.

Figure 2:
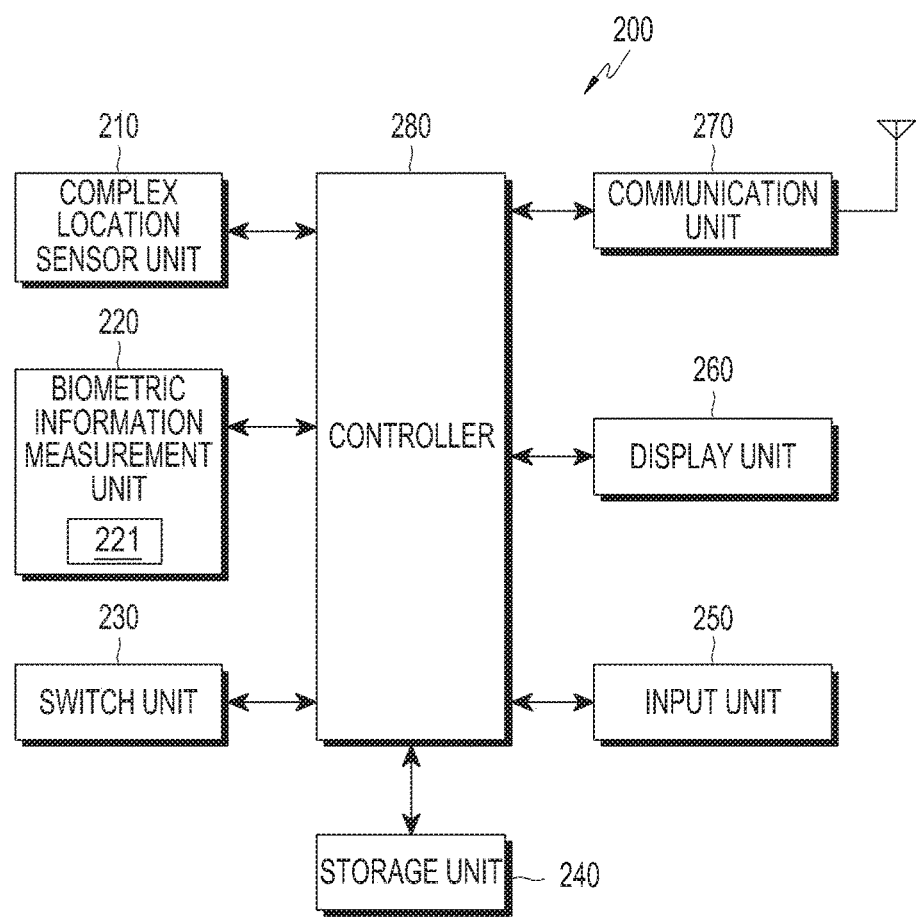
FIG. 2 is a block diagram schematically illustrating an electronic device for measuring biometric information according to various embodiments of the present disclosure.

FIG. 2 is a block diagram schematically illustrating an electronic device for measuring biometric information according to various embodiments of the present disclosure.

Referring to FIG. 2, an electronic device 200 may include, for example, all or a part of the electronic device 101 illustrated in FIG. 1. The electronic device 200 according to various embodiments of the present disclosure may include a complex location sensor unit 210, a biometric information measurement unit 220, a switch unit 230, and a controller 280. Further, the electronic device 200 may further include a storage unit 240, an input unit 250, a display unit 260, and a communication unit 270.

The complex location sensor unit 210 may detect a plurality of pieces of location information (or a plurality of pieces of sensor information for calculating one piece of position (and/or location) information) on a measurement point. The complex location sensor unit 210 may include a plurality of location-based sensors, and may detect each of a plurality of pieces of location information (or a plurality of pieces of sensor information for calculating one piece of position (and/or location) information) on the measurement point from the plurality of location-based sensors. According to an embodiment of the present disclosure, the plurality of pieces of location information may include an acceleration value, a geomagnetic value, and an altitude value. Further, the plurality of pieces of location information may include location-based detection values detected from all the location-based sensors, such as a gyro detection value, an acceleration detection value, and a motion detection value, but are not limited thereto. The controller 280 may recognize a location and attitude of the electronic device 200 in the measurement point based on the plurality of pieces of location information detected by the complex location sensor unit 210 and determine a location, a direction, a polarity, and a channel of each of a plurality of electrodes according to the recognized location and attitude of the electronic device 200.

The biometric information measurement unit 220 may detect biometric information which an examinee desires to measure through a plurality of electrodes having an electrode array electrically connected thereto.

The electrode array includes locations, directions, polarities and/or the arrangement of electrode channels of the plurality of electrodes. For example, the electrode array may include a location, a direction, and/or a polarity arrangement of each electrode. The electrode array may include the arrangement of a current electrode channel to which the current is applied and/or a voltage electrode channel for measuring the voltage.

According to an embodiment of the present disclosure, the biometric information measurement unit 220 may detect biometric information (for example, a biometric signal) of the examinee from the plurality of electrodes of the preset electrode array controlled from the recognized electrode array according to the location and the attitude of the electronic device 200 recognized in the measurement point. According to an embodiment of the present disclosure, the biometric information measurement unit 220 may include a biometric signal measurement module 221 for detecting a biometric signal. The biometric signal measurement module 221 may detect the biometric signal of the examinee by placing the electronic device 200 at a certain location according to the biometric signal to be measured. For example, the biometric signal may include an electrocardiography (ECG) signal, an electroencephalogram (EEG) signal, an electrooculogram (EOG) signal, an electrogastrogram (EGG) signal, and an electromyography (EMG) signal.

The switch unit 230 may include a plurality of switches (or one switch including at least one input port and at least one output port) corresponding to the plurality of electrodes, respectively, and may electrically connect the plurality of electrodes and the biometric information measurement unit 220 through the plurality of switches. The switch unit 230 may be controlled to change the electrode array connected between the plurality of electrodes and the biometric information measurement unit 220 according to a control of the controller 280.

The controller 280 may recognize the electrode array of the plurality of electrodes formed in the electronic device 200 based on the plurality of pieces of location information detected in the measurement point and switch the recognized electrode array to correspond to a preset electrode array by controlling the switch unit 230. The controller 280 may analyze the biometric information detected by the biometric information measurement unit 220 electrically connected through the changed electrode array.

The controller 280 may recognize an electrode array of a plurality of electrodes according to a location and attitude of the electronic device 200 based on a plurality of pieces of location information detected by the complex location sensor unit 210 and, when at least one of the location, direction, polarity, and channel of at least one electrode is different from a preset electrode array based on a comparison between the recognized electrode array and the preset electrode array, change the electrode array of the plurality of electrodes such that the recognized electrode array of the plurality of electrodes corresponds to the preset electrode array of the plurality of electrodes. The controller 280 may detect the biometric information of the examinee from the biometric information measurement unit 220 through the changed electrode array of the plurality of electrodes.

For example, when two electrodes (for example, A and B) are formed on the rear surface of the electronic device 200 (see FIG. 4) and left and right directions and the polarity of each electrode are preset as the electrode array of the two electrodes, it is assumed that the electrode A is set as a (−) electrode in a left direction of the examinee and the electrode B is set as a (+) electrode in a right direction of the examinee. When the user or examinee places the electronic device 200 on the corresponding body part to measure the biometric information, if the preset left and right directions of the electronic device 200 are changed, the controller 280 may recognize that left and right directions of the two electrodes (A and B) of the electronic device 200 are also changed and control and change the switch unit 230 to make the electrode array of the recognized two electrodes (A and B) correspond to the preset electrode array, that is, to connect the electrode A in a right direction of the examinee as a (+) electrode and the electrode B in a left direction of the examinee as a (−) electrode.

The storage unit 240 may store in advance electrode array information on each electrode and basic information of the examinee. The electrode array information may include a location, direction, polarity, and arrangement of the electrode channel of each electrode. The basic information may include a name, an age, a gender, a height, and a weight of the examinee.

The input unit 250 may receive various input signals generated or input by the user or examinee. According to an embodiment of the present disclosure, the input unit 250 may include a key pad, a touch pad, and a voice input module, such as a microphone. Further, the input unit 250 is not limited thereto and may include all input means which can make an input into the electronic device 200 according to various embodiments of the present disclosure.

The display unit 260 may display, on a screen, a health state analysis result analyzed based on the biometric information detected by the biometric information measurement unit 220 through the electrode array of the plurality of electrodes controlled by the controller 280. For example, the health state analysis result may include a biometric index analyzed based on the biometric signal detected by the biometric information measurement unit 220. According to an embodiment of the present disclosure, when the detected biometric information is the biometric signal, the display unit 260 may display, on the screen, the biometric index, such as a heartrate, a heart period, a standard deviation of the heart period, a pulse, arrhythmia, an impedance blood volume, and a stress index, analyzed from a parameter in a time domain of the biometric signal.

The communication unit 270 may receive information required for measuring the biometric information according to the present disclosure from the outside. For example, the communication unit 270 may receive an average stress index according to the age and the gender of the examinee from the outside (for example, the server 106).

The controller 280 may overall control the electronic device 200 according to various embodiments of the present disclosure. The controller 280 may recognize the location and attitude of the electronic device 200 based on the plurality of pieces of location information detected through the complex location sensor unit 210, determine whether the electrode array of the plurality of electrodes formed in the electronic device 200 is changed according to the recognized location and attitude, and, when the electrode array of the plurality of electrodes is changed from the preset electrode array, change the electrode array of the plurality of electrodes recognized in the current measurement point into the preset electrode array through the switch unit 230. Further, the controller 280 may analyze health state information based on a plurality of pieces of biometric information detected through the plurality of electrodes having the electrode array which can be changed according to the recognized electrode array.

Figure 3:
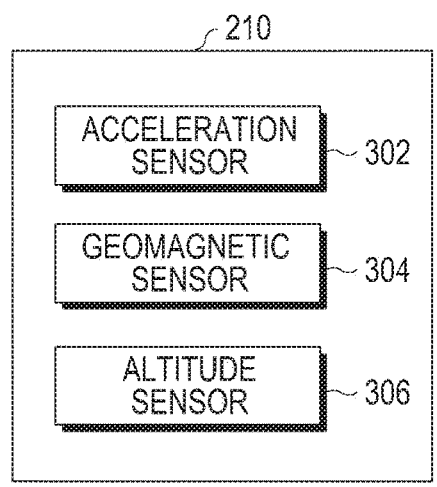
FIG. 3 is a block diagram illustrating a complex location sensor unit according to various embodiments of the present disclosure.
Figure 4:
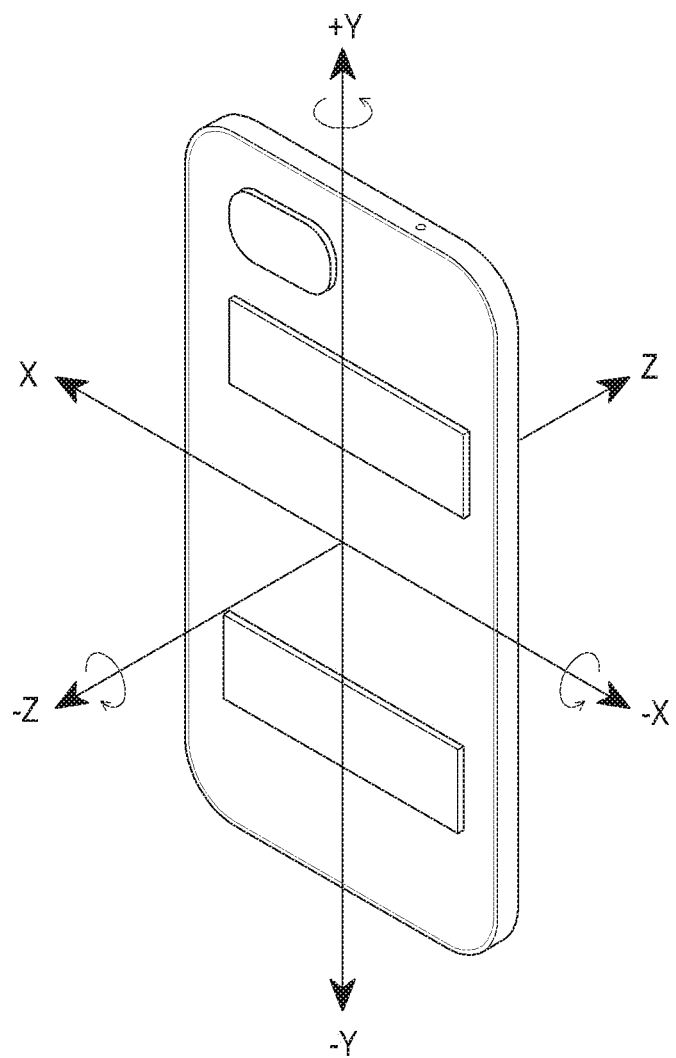
FIG. 4 illustrates a reference direction of an electronic device according to various embodiments of the present disclosure.

FIG. 3 is a block diagram illustrating a complex location sensor unit according to various embodiments of the present disclosure, and FIG. 4 illustrates a reference direction of an electronic device according to various embodiments of the present disclosure.

Referring to FIGS. 3 and 4, the complex location sensor unit 210 may include an acceleration sensor 302, a geomagnetic sensor 304, and an altimeter sensor 306.

The acceleration sensor 302 may detect an acceleration value in a measurement point when the electronic device 200 moves. According to the present disclosure, the acceleration sensor 302 may have three axes including a Y axis corresponding to a major axis length direction of the electronic device 200 based on the center of the electronic device 200, an X axis corresponding to a minor axis length direction of the electronic device 200, and a Z axis corresponding to a direction orthogonal to the plane (for example, the screen) with the X axis and the Y axis as illustrated in FIG. 4, and it is assumed that directions of the X axis, the Y axis, and the Z axis of the electronic device 200 are set as reference directions in a state where the Y axis is orthogonal to the horizontal plane, and the X axis and the Z axis are parallel to the horizontal plane. For example, the acceleration sensor 302 may have reference directions including an upward direction from the center of the electronic device 200, which is a +Y axis (a direction opposite thereto is a −Y axis), a rightward direction from the center of the electronic device 200, which is a +X axis (a direction opposite thereto is an −X axis), and a forward direction from the center of the electronic device 200, which is a +Z axis (a direction opposite thereto is a −Z axis).

The geomagnetic sensor 304 may detect a direction angle of the electronic device 200 by Earth's magnetic field in a measurement point where the electronic device 200 is located. According to the present disclosure, the geomagnetic sensor 304 may have reference angles having rotation angles (that is, direction angles) (for example, a pitch angle, a roll angle, and a yaw angle) of 0 degrees with respect to the X axis, the Y axis, and the Z axis of the electronic device 200 in a state where the geomagnetic sensor 304 has three axes equal to those of the acceleration sensor 302, and the Y axis is orthogonal to the horizontal plane and the X and Z axes are parallel to the horizontal plane as illustrated in FIG. 4. The controller 280 may recognize an attitude angle of the electronic device 200 through the geomagnetic value detected by the geomagnetic sensor 304.

The altimeter sensor 306 may detect an altitude (height) of the electronic device 200 by an air pressure at a measurement point where the electronic device 200 is located.

When the electronic device 200 measures biometric information in the measurement point, the controller 280 may recognize a direction, an angle, and an altitude for each axis in the measurement point based on the reference direction and angle for each axis of the complex location sensor unit 210, and thus recognize the location and attitude of the electronic device 200. Further, the controller 280 may determine locations and directions of a plurality of electrodes formed on at least one surface of the electronic device 200 according to the recognized location and attitude of the electronic device 200, and thus determine whether preset locations and directions of the plurality of electrodes are changed.

As described above, the controller 280 may recognize the location and attitude of the electronic device 200 in the measurement point based on the reference direction and the reference angle of each axis of the complex location sensor unit 210 by complexly using the plurality of pieces of location information (for example, the acceleration value, the geomagnetic value, and the altitude value) detected by the complex location sensor unit 210 and a combination thereof and, determine whether the electrode array (that is, the location, direction, polarity, and electrode channel arrangement) of the plurality of electrodes in the measurement point is changed according to the recognized location and attribute, and change the electrode array of the plurality of electrodes according to a result of the determination.

In FIG. 3, the complex location sensor unit 210 includes the acceleration sensor 302, the geomagnetic sensor 304, and the altimeter sensor 306, but the present disclosure is not limited thereto and the complex location sensor unit 210 may include all location-based sensors, such as a gyro sensor, an angular speed sensor, and a motion sensor.

Figure 5:
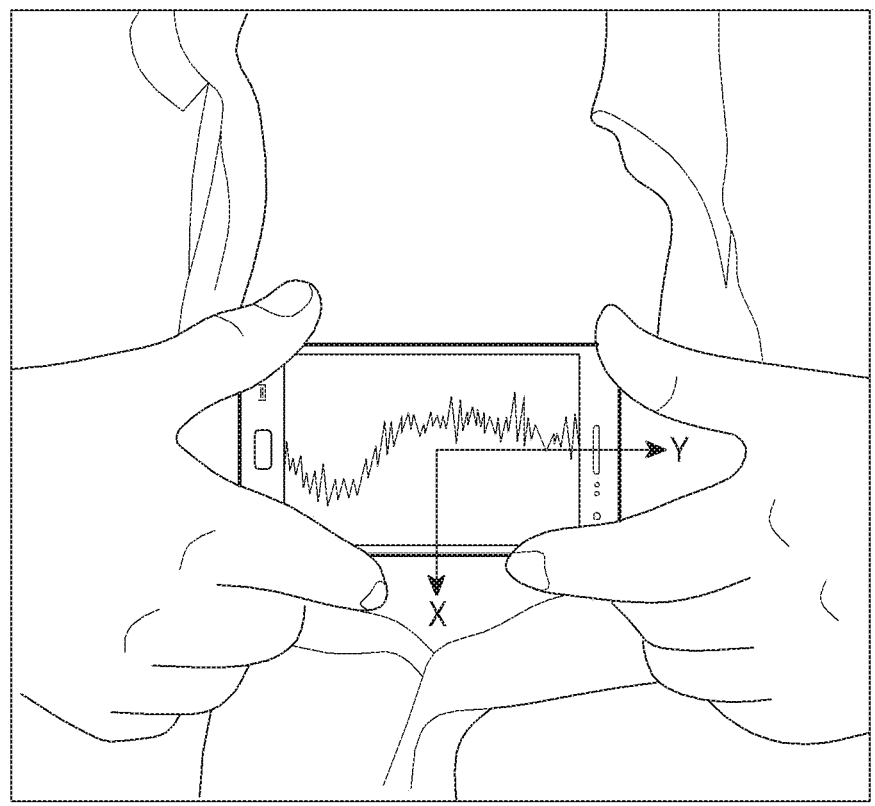
FIG. 5 illustrates a mounting of an electronic device on a body part according to various embodiments of the present disclosure.

FIG. 5 illustrates a mounting of an electronic device on a body part according to various embodiments of the present disclosure.

Referring to FIG. 5, the electronic device 200 may measure a biometric signal by mounting two electrodes (electrode A and electrode B) formed on the rear surface of the electronic device 200 illustrated in FIG. 4 on a chest part to measure the biometric signal. For example, the biometric signal may be an ECG signal, and it may be assumed that the electrode A is set as the (−) polarity in a left direction of the examinee and the electrode B is set as the (+) polarity in a right direction of the examinee. In this case, the biometric signal as illustrated in FIG. 5 may be measured. Further, according to the present disclosure, even though left and right directions of the electronic device 200 are exchanged, that is, two electrodes are reversed, it is possible to detect the biometric information as illustrated in FIG. 5 by controlling the switch unit 230 to change locations and attitudes of the plurality of electrodes (A and B) into preset locations and attitudes according to the location and attitude of the electronic device 200 in a current measurement point.

Figure 6:
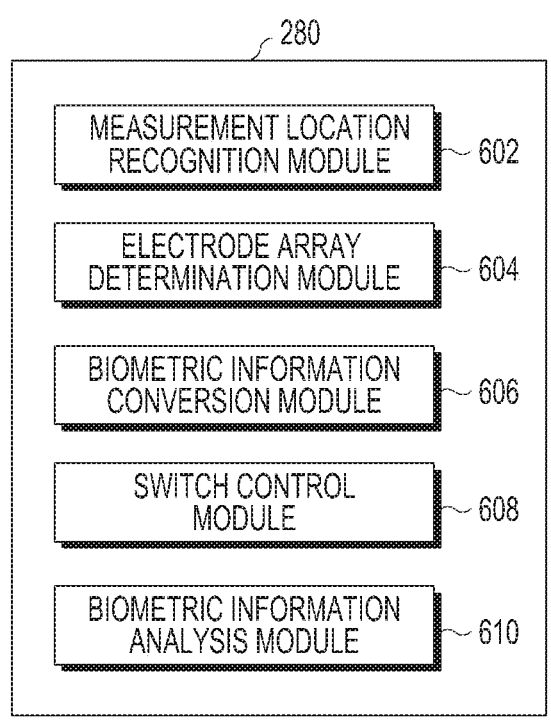
FIG. 6 is a block diagram illustrating a controller according to various embodiments of the present disclosure.

FIG. 6 is a block diagram illustrating a controller according to various embodiments of the present disclosure.

Referring to FIG. 6, the controller 280 may include a measurement location recognition module 602, an electrode array determination module 604, a switch control module 608, and a biometric information analysis module 610.

The measurement location recognition module 602 may recognize the electrode array of the plurality of electrodes in the measurement point based on the plurality of pieces of location information (for example, the acceleration value, the geomagnetic value, and the altitude value) detected in the measurement point by the complex location sensor unit 210.

The measurement location recognition module 602 may first recognize the location and attitude of the electronic device 200 based on the pieces of location information detected in the measurement point. The measurement location recognition module 602 may calculate the direction and the angle of each axis changed from the reference direction and the reference angle of each axis of the complex location sensor unit 210 by using the acceleration value and the geomagnetic value detected in the measurement point and recognize the location and the attitude of the electronic device 200 based on the location information including an altitude according to the altitude value detected in the measurement point.

The electrode array determination module 604 may recognize the electrode array (for example, the location, direction, polarity, and electrode channel arrangement of each electrode) of the plurality of electrodes formed on at least one surface of the electronic device 200 according to the recognized location and attitude of the electronic device 200.

The electrode array determination module 604 may compare the electrode array of the plurality of electrodes according to the location and the attitude of the electronic device 200 recognized by the measurement location recognition module 602 with a preset electrode array of the plurality of electrodes, and determine whether the recognized electrode array is changed from the preset electrode array.

When there is a change in the location, direction, polarity, and electrode channel of at least one of the plurality of electrodes, the electrode array determination module 604 may determine that the recognized electrode array is changed.

When the electrode array determination module 604 determines that the recognized electrode array is changed, the switch control module 608 may control the switch unit 230 to make the recognized electrode array correspond to the preset electrode array. For example, the switch control module 608 may switch the switch unit 230 including a plurality of switches (or one switch including at least one input port and at least one output port) corresponding to the plurality of electrodes, respectively, and make a control to connect the preset electrode array to the biometric information measurement unit 220.

In the reference direction and the reference angle of the electronic device 200, the polarity of each electrode may be preset according to the location and the direction of each electrode. For example, it is assumed that the polarity of the left electrode A is set as (−) and the polarity of the right electrode B is set (+) in the reference direction and the reference angle of the electronic device 200. When the electronic device 200 has a change from the reference direction and the reference angle in the measurement point, the electrode array of the plurality of electrodes, that is, the location, direction, polarity, and electrode channel arrangement of each electrode may be changed according to the location and the attitude of the changed electronic device 200.

The switch control module 608 may compare the changed electrode array with a preset electrode array and control the switch unit 230 such that the changed electrode array corresponds to the preset electrode array. For example, when left and right directions of the left electrode A and the right electrode B are exchanged, the switch control module 608 may switch a switch corresponding to the corresponding electrode A to connection the left electrode A having the (+) polarity changed from the (−) polarity preset to the left electrode A to the biometric information measurement unit 220 and switch a switch corresponding to the corresponding electrode B to connect the right electrode B having the (−) polarity changed from the (+) polarity preset to the right electrode B to the biometric information measurement unit 220. Accordingly, the user or examinee can detect accurate biometric information (for example, biometric signal) regardless of the change in the location and the attitude of the electronic device 200.

The biometric information analysis module 610 may analyze the biometric information detected by the biometric information measurement unit 220 through the electrode array of the plurality of electrodes controlled by the switch control module 608. According to an embodiment of the present disclosure, the biometric information analysis module 610 may analyze the biometric information, that is, the biometric signal detected by the biometric information measurement unit 220. For example, the biometric information analysis module 610 may analyze biometric indexes, such as a heartrate, a heart period, a standard deviation of the heart period, a pulse, a number of arrhythmia occurrences, an impedance blood volume, and a stress index, from a parameter in a time domain of the detected biometric signal.

Meanwhile, the controller 280 may further include a biometric information conversion module 606 that converts the biometric information detected through the changed electrode array to correspond to the biometric information detected through the preset electrode array instead of the switch control module 608.

When there is the change in the electrode array of the plurality of electrodes recognized according to the location and the attitude of the electronic device 200 recognized in the measurement point, the biometric information conversion module 606 may convert and output the biometric signal detected through the recognized electrode array without controlling the recognized electrode array through the switch control module 608. For example, when it is determined that the recognized electrode array is changed, the biometric information conversion module 606 may convert the detected biometric signal to compensate for a difference between the recognized electrode array and the preset electrode array.

According to an embodiment of the present disclosure, the electronic device for measuring biometric information may include a complex location sensor unit configured to detect a plurality of pieces of location information in a measurement point, a biometric information measurement unit configured to detect biometric information through a plurality of electrodes formed on at least one surface of the electronic device, a switch unit electrically connected to the biometric information measurement unit and including a plurality of switches corresponding to the plurality of electrodes, respectively, and a controller configured to recognize an electrode array of the plurality of electrodes according to an attitude of the electronic device in the measurement point based on the plurality of pieces of detected location information and control the switch unit such that the recognized electrode array corresponds to a preset electrode array.

According to an embodiment of the present disclosure, the complex location sensor unit may include an acceleration sensor configured to detect an acceleration value in the measurement point, a geomagnetic sensor configured to detect a geomagnetic value in the measurement point, and an altitude sensor configured to detect an altitude value in the measurement point.

According to an embodiment of the present disclosure, the biometric information measurement unit may include a biometric signal measurement module configured to detect a biometric signal of the examinee.

According to an embodiment of the present disclosure, the biometric signal measurement module may detect one of an ECG signal, an EEG signal, an EOG signal, an EGG signal, and an EMG signal.

According to an embodiment of the present disclosure, the controller may include a measurement location recognition module configured to recognize a location and an attitude of the electronic device in the measurement point by using the plurality of pieces of detected location information, an electrode array determination module configured to recognize the array of the plurality of electrodes according to the recognized location and attitude of the electronic device, compare the recognized electrode array and the preset electrode array, and determine whether the electrode array is changed, and a switch control module configured to control the switch unit to make the recognized electrode array correspond to the preset electrode array and to connect the electrode array to the biometric information measurement unit based on a result of the determination.

According to an embodiment of the present disclosure, the measurement location recognition module may calculate a direction and an angle of each axis changed from a reference direction and a reference angle of each axis of the complex location sensor unit by using the detected acceleration value and geomagnetic value and recognize the location and the attitude of the electronic device based on the calculated direction and angle of each axis and the detected altitude value.

According to an embodiment of the present disclosure, the electrode array determination module may compare whether the recognized electrode array of each electrode matches the preset electrode array of the corresponding electrode and, when the recognized electrode array of at least one electrode is not equal to the preset electrode array of the corresponding electrode, determine that the recognized electrode array is changed.

According to an embodiment of the present disclosure, when the recognized electrode array is changed, the switch control module may switch a corresponding switch to connect the preset electrode array of the corresponding electrode changed from the changed electrode array of the corresponding electrode to the biometric information measurement unit.

According to an embodiment of the present disclosure, the electrode array may include a location, direction, polarity, arrangement of electrode channels of each electrode.

According to an embodiment of the present disclosure, the controller may further include a biometric information analysis module configured to analyze health state information of the examinee by analyzing the biometric information detected through the controlled electrode array of the plurality of electrodes.

According to an embodiment of the present disclosure, the biometric information analysis module may analyze a biometric index of the examinee based on the detected biometric signal.

According to an embodiment of the present disclosure, the controller may further include a biometric information conversion module configured to, when the recognized electrode array is changed, convert the detected biometric signal to compensate for a difference between the recognized electrode array and the present electrode array.

According to an embodiment of the present disclosure, the biometric information analysis module may analyze a biometric index of the examinee based on the converted biometric signal.

Figure 7:
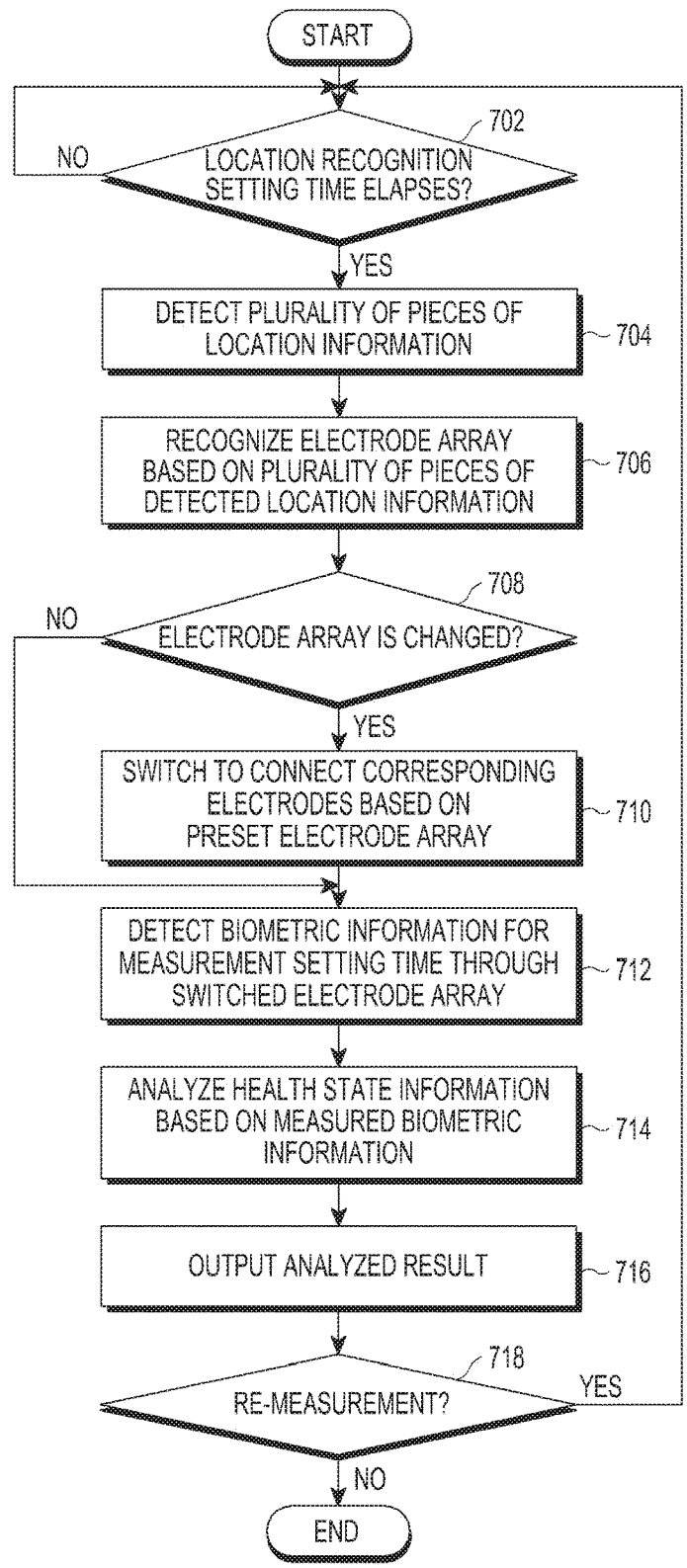
FIG. 7 is a flowchart illustrating a method of measuring biometric information according to various embodiments of the present disclosure.

FIG. 7 is a flowchart illustrating a method of measuring biometric information according to various embodiments of the present disclosure. In FIG. 7, a method of measuring biometric information (for example, a biometric signal) through a change in an electrode array is described according to various embodiments of the present disclosure.

Referring to FIG. 7, the measurement location recognition module 602 of the controller 280 may determine whether a location recognition setting time (for example, 3 seconds) elapses in operation 702. When the location recognition setting time elapses, the measurement location recognition module 602 may detect a plurality of pieces of location information through the complex location sensor unit 210 at the location (measurement point) of the corresponding electronic device 200 in operation 704. When the location recognition setting time does not elapse in operation 702, the measurement location recognition module 602 returns to operation 702 and repeats the following operations.

The measurement location recognition module 602 of the controller 280 may recognize the location and the attitude of the electronic device 200 based on the plurality of pieces of detected location information, and recognize the electrode array of the plurality of electrodes in the measurement point according to the recognized location and attitude in operation 706. Thereafter, the electrode array determination module 604 may determine whether the recognized electrode array is changed from the preset electrode array in operation 708.

When the recognized electrode array is changed in operation 708, the switch control module 608 of the controller 280 may control a plurality of switches to make the recognized electrode array correspond to the preset electrode array and connect to the biometric information measurement unit 220 in operation 710. Meanwhile, when the recognized electrode array has no change in operation 708, the controller 280 proceeds to operation 712.

The biometric information analysis module 610 of the controller 280 may detect, in operation 712, biometric information from the biometric information measurement unit 220 for a measurement setting time through the electrode array controlled in operation 710, and analyze health state information based on the detected biometric information in operation 714. For example, the biometric information may include various biometric signals, such as an ECG signal, an EEG signal, an EOG signal, an EGG signal, and an EMG signal. Further, the health state information may include various biometric indexes, such as a heartrate, a heart period, a standard deviation of the heart period, a pulse, arrhythmia, an impedance blood volume, and a stress index, from a parameter in a time domain of the detected biometric signal.

The controller 280 may output a result (for example, a biometric index related to the detected biometric signal) analyzed by the biometric information analysis module 610 on the screen of the display unit 260 in operation 716.

Thereafter, the controller 280 may determine whether a re-measuring signal for measuring the biometric information again is input in operation 718. When the re-measuring signal is input, the controller 280 may return to operation 702 and repeat the following operations. When a re-measuring end signal is input in operation 718, the controller 280 may end the measurement of the biometric information.

Figure 8:
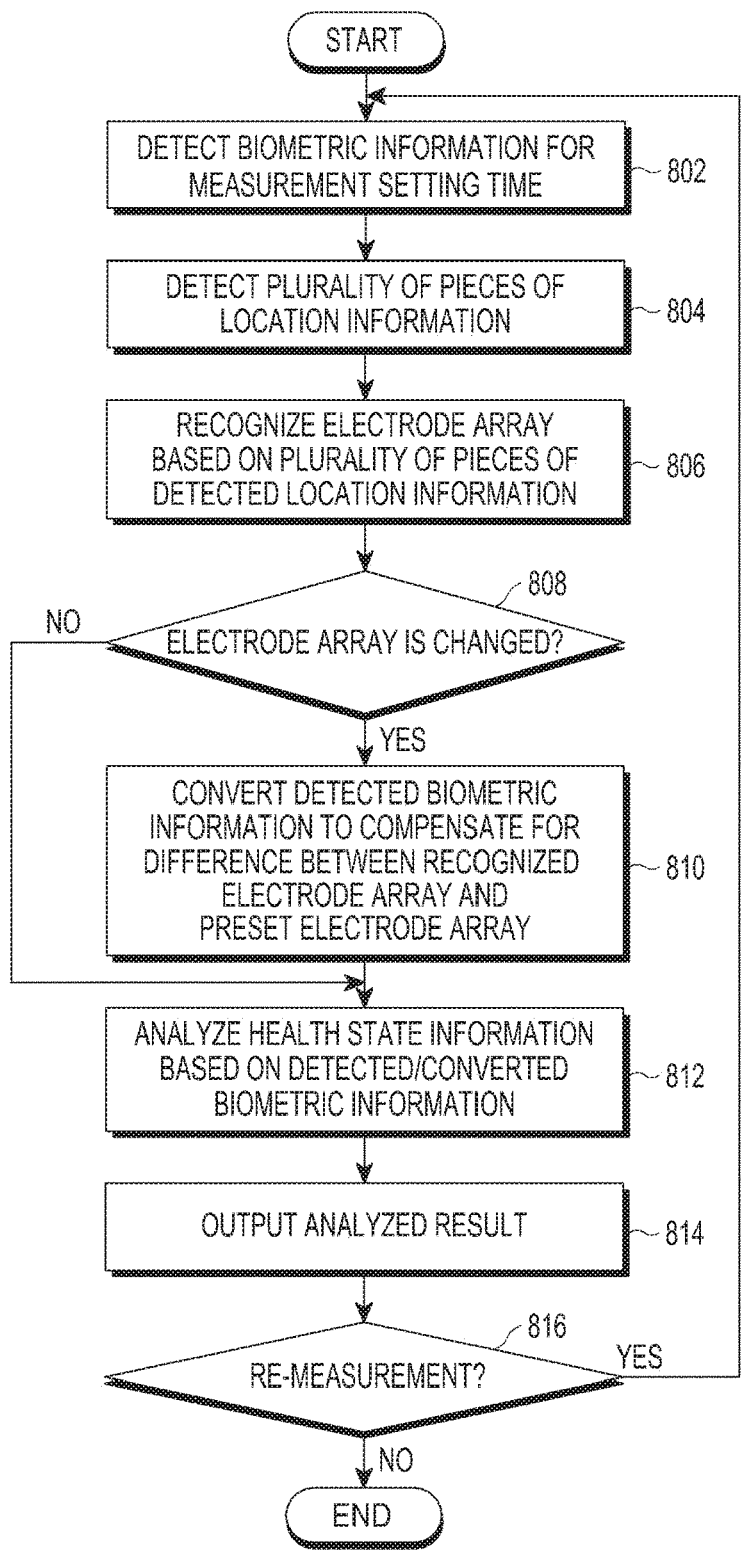
FIG. 8 is a flowchart illustrating a method of measuring biometric information according to various embodiments of the present disclosure.

FIG. 8 is a flowchart illustrating a method of measuring biometric information according to various embodiments of the present disclosure. In FIG. 8, a method of measuring biometric information through biometric information conversion is described according to various embodiments of the present disclosure.

Referring to FIG. 8, the controller 280 detects biometric information through the biometric information measurement unit 220 for a measurement setting time in operation 802.

The controller 280 recognizes a point where the biometric information is detected as a measurement point and detects a plurality of pieces of location information through the complex location sensor unit 210 in the measurement point in operation 804. For example, the plurality of pieces of location information may include an acceleration value, a geomagnetic value, and an altitude value.

The measurement location recognition module 602 of the controller 280 may recognize the location and the attitude of the electronic device 200 based on the plurality of pieces of detected location information, and recognize the electrode array of the plurality of electrodes in the measurement point according to the recognized location and attitude in operation 806. Thereafter, the electrode array determination module 604 may determine whether the recognized electrode array is changed from the preset electrode array in operation 808.

Figure 9A:
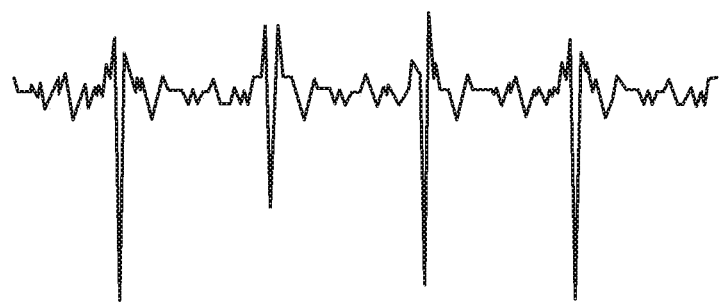
FIG. 9A illustrates a display screen showing biometric information before biometric information is converted after an electrode array is changed according to various embodiments of the present disclosure.
Figure 9B:
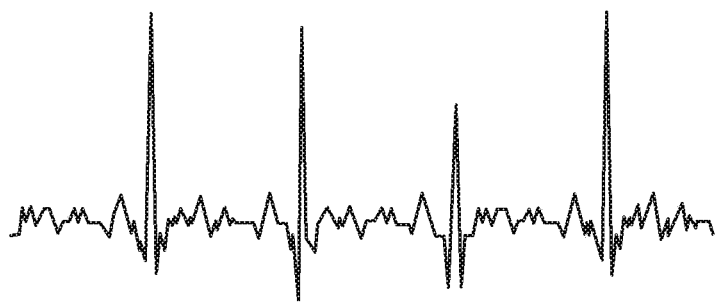
FIG. 9B illustrates a display screen showing biometric information after biometric information is converted after an electrode array is changed according to various embodiments of the present disclosure.

When the recognized electrode array has the change in operation 808, the biometric information conversion module 606 of the controller 280 may convert the recognized electrode array to compensate for a difference between the recognized electrode array and the preset electrode array in operation 810. For example, when preset electrode polarities are exchanged according to left and right directions of the electrodes, the biometric information (for example, biometric signal) detected through the recognized electrode array may be output as illustrated in FIG. 9A. In this case, the biometric information conversion module 606 may multiply the biometric signal (see FIG. 9A) detected through the electrode array having the exchanged electrode polarities by the error, that is, −1 as the compensation for the polarity reversal according to the left and right directions and thus convert the biometric signal of FIG. 9A into a normal biometric signal which is vertically reversed as illustrated in FIG. 9B. Meanwhile, when the recognized electrode array has no change in operation 808, the controller 280 proceeds to operation 812.

In operation 812, the biometric information analysis module 610 of the controller 280 may analyze the health state information based on the biometric information converted in operation 810 or detected in operation 802. For example, the biometric information may include various biometric signals, such as an ECG signal, an EEG signal, an EOG signal, an EGG signal, and an EMG signal. Further, the health state information may include various biometric indexes, such as a heartrate, a heart period, a standard deviation of the heart period, a pulse, arrhythmia, an impedance blood volume, and a stress index, from a parameter in a time domain of the detected biometric signal.

The controller 280 may output a result (for example, a biometric index related to the detected/converted biometric signal) analyzed by the biometric information analysis module 610 on the screen of the display unit 260 in operation 814.

Thereafter, the controller 280 may determine whether a re-measuring signal for measuring the biometric information again is input in operation 816. When the re-measuring signal is input, the controller 280 may return to operation 802 and repeat the following operations. When a re-measuring end signal is input in operation 816, the controller 280 may end the measurement of the biometric information.

According to an embodiment of the present disclosure, a method of measuring biometric information by an electronic device may include a process of detecting a plurality of pieces of location information in a measurement point, a process of recognizing an electrode array of a plurality of electrodes formed on at least one surface of the electronic device according to an attitude of the electronic device in the measurement point based on the plurality of pieces of detected location information, a process of determining whether the recognized electrode array is changed by comparing the recognized electrode array and a preset electrode array, and a process of controlling a switch unit including a plurality of switches corresponding to the plurality of electrodes, respectively, such that the recognized electrode array corresponds to the preset electrode array and is connected to a biometric information measurement unit based on a result of the determination.

According to an embodiment of the present disclosure, the process of recognizing the array of the plurality of electrodes may include a process of detecting an acceleration value, a geomagnetic value, and an altitude value of the electronic device in a measurement point by a complex location sensor unit, a process of calculating a direction and an angle of each axis changed from a reference direction and a reference angle of each axis of the complex location sensor unit by using the detected acceleration value and geomagnetic value, a process of recognizing a location and an attitude of the electronic device from the calculated direction and angle of each axis and the detected altitude value, and a process of recognizing the electrode array of the plurality of electrodes according to the recognized location and attitude of the electronic device.

According to an embodiment of the present disclosure, the process of determining whether the recognized electrode array is changed may include a process of comparing whether the recognized electrode array of each electrode matches the preset electrode array of the corresponding electrode and, when the recognized electrode array of at least one electrode is not equal to the preset electrode array of the corresponding electrode based on a result of the comparison, determining that the recognized electrode array is changed.

According to an embodiment of the present disclosure, when the recognized electrode array is changed, the process of controlling the switch unit may include a process of switching a corresponding switch to connect the preset electrode array of the corresponding electrode changed from the changed electrode array of the corresponding electrode to the biometric information measurement unit.

According to an embodiment of the present disclosure, the electrode array may include a location, direction, polarity, arrangement of electrode channels of each electrode.

According to an embodiment of the present disclosure, the method of measuring the biometric information by the electronic device may further include a process of analyzing health state information of an examinee by detecting biometric information through the plurality of electrodes by the biometric information measurement unit.

According to an embodiment of the present disclosure, the process of analyzing the health state information of the examinee may include a process of analyzing a biometric index of the examinee based on a biometric signal detected through the plurality of electrodes of the controlled electrode array by the biometric information measurement unit.

According to an embodiment of the present disclosure, when the method of measuring the biometric information by the electronic device may further include, when the recognized electrode array is changed, a process of converting the detected biometric signal to compensate for a difference between the recognized electrode array and the preset electrode array.

According to an embodiment of the present disclosure, the process of analyzing the health state information of the examinee may include a process of analyzing a biometric index of the examinee based on a biometric signal detected by the biometric information measurement unit through the plurality of electrodes of the recognized electrode array.

FIG. 9A illustrates a display screen showing biometric information before the biometric information conversion after an electrode array change according to various embodiments of the present disclosure, and FIG. 9B illustrates a display screen showing biometric information after the biometric information conversion after an electrode array change according to various embodiments of the present disclosure.

Referring to FIGS. 9A and 9B, when the recognized electrode array in the measurement point is changed from the preset electrode array (for example, when preset electrode polarities are reversed according to left and right directions of the electrodes), the signal illustrated in FIG. 9A corresponds to an example of the biometric information (for example, the biometric signal) detected by the biometric information measurement unit 220 through the plurality of electrodes having the changed electrode array. The signal illustrated in FIG. 9B corresponds to an example of the signal converted through the compensation for the error between the preset electrode array and the changed electrode array in operation 810 of FIG. 8. As illustrated in FIGS. 9A and 9B, it is possible to acquire accurate biometric information regardless of the electrode array by converting corresponding measurement information without physically changing the changed electrode array.

For example, according to an embodiment of the present disclosure, it is possible to acquire accurate biometric information regardless of the electrode array (electrode location, direction, polarity, and channel) by changing the changed electrode array in hardware by using the switch control module 608 as illustrated in operation 710 of FIG. 7 or converting the biometric information according to the changed electrode array in software by using the biometric information conversion module 606 as illustrated in operation 810 of FIG. 8 and compensating for the error.

Figure 10A:
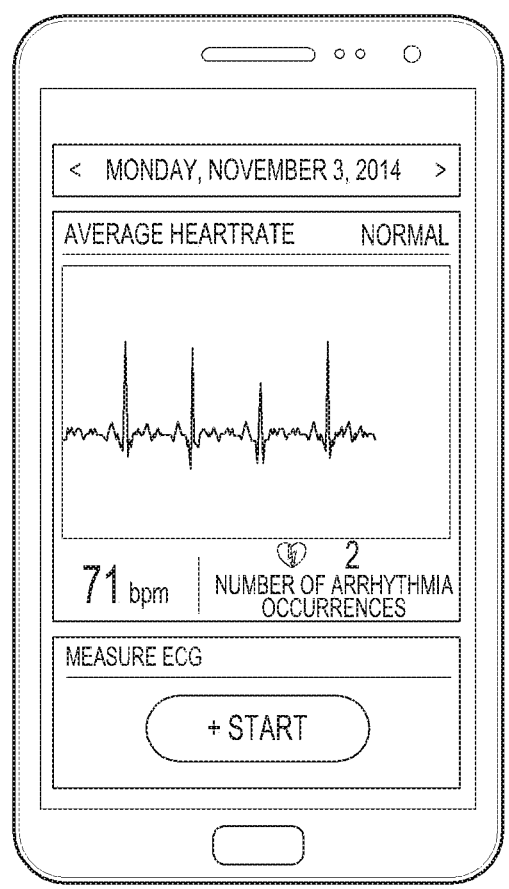
FIGS. 10A, 10B, and 10C illustrate a display screen showing biometric information measurement results according to various embodiments of the present disclosure.
Figure 10B:
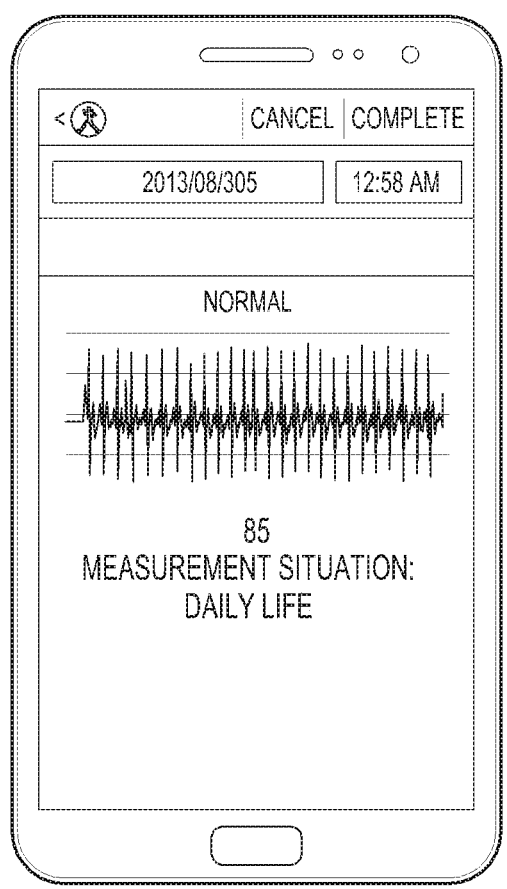
Figure 10C:
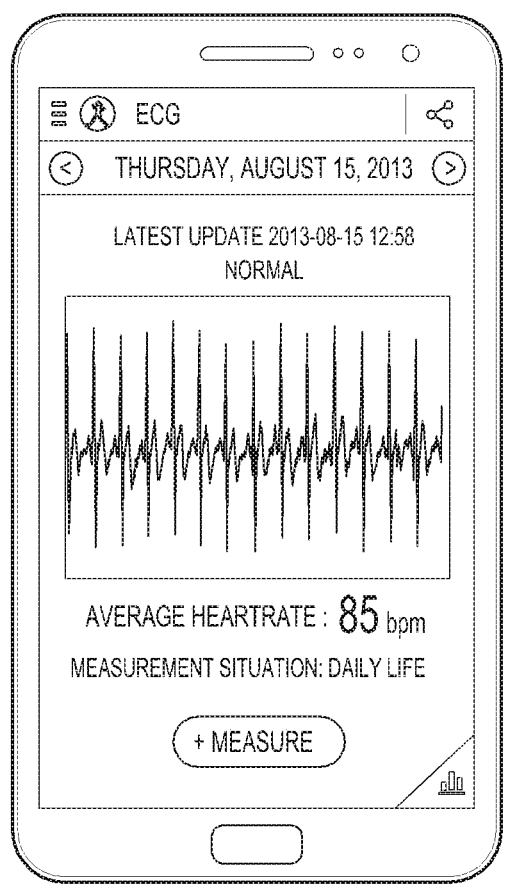

FIGS. 10A, 10B, and 10C illustrate a display screen showing biometric information measurement results according to various embodiments of the present disclosure.

Referring to FIGS. 10A, 10B, and 10C, an ECG signal is illustrated as an example of the detected biometric information according to an embodiment of the present disclosure. As illustrated in FIG. 10A, an average heartrate and a number of arrhythmia occurrences may be displayed on the screen of the display unit 260 along with the detected ECG signal. Alternatively, as illustrated in FIGS. 10B and 10C, a measurement situation (for example, daily life), a recent update date (for example, 2013-08-15), and simple health state information (for example, normal) may be displayed along with the detected ECG signal.

Figure 11A:
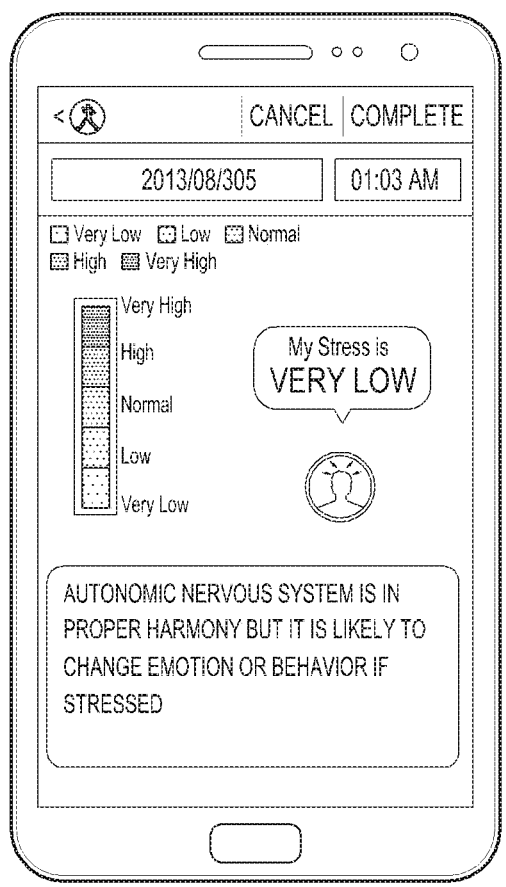
FIGS. 11A and 11B illustrate a display screen showing biometric information analysis results according to various embodiments of the present disclosure.
Figure 11B:
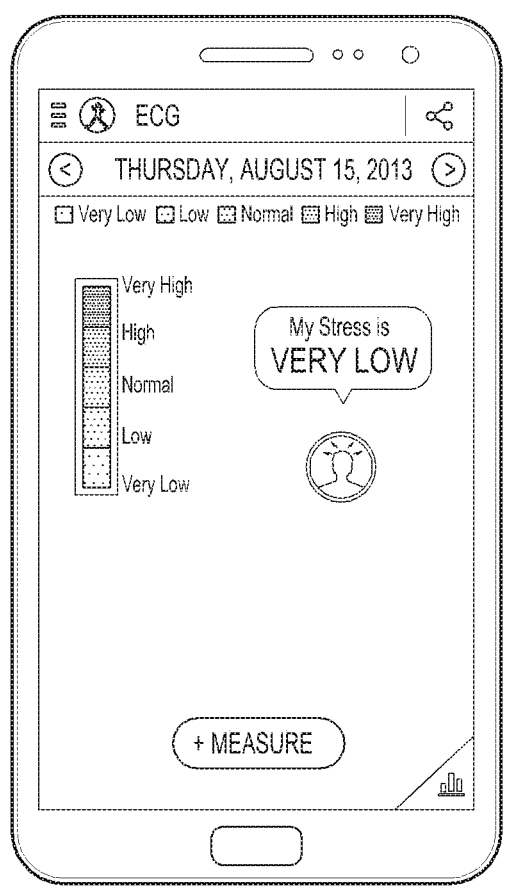

FIGS. 11A and 11B illustrate a display screen showing biometric information analysis results according to various embodiments of the present disclosure.

Referring to FIGS. 11A and 11B, the detected biometric information according to an embodiment of the present disclosure may be analyzed and health state information, such as biometric indexes, may be displayed in various forms. As illustrated in FIG. 11A, a health state of the examinee may be displayed through a bar graph with different colors according to the biometric index (for example, stress index) and in the form of text. Further, an area for explaining the health state indicated by the biometric index may be further displayed. In addition, as illustrated in FIG. 11B, a measurement button for measuring the biometric information again by the user or examinee or measuring biometric information on a new examinee may be also displayed on the analysis result screen.

Figure 12:
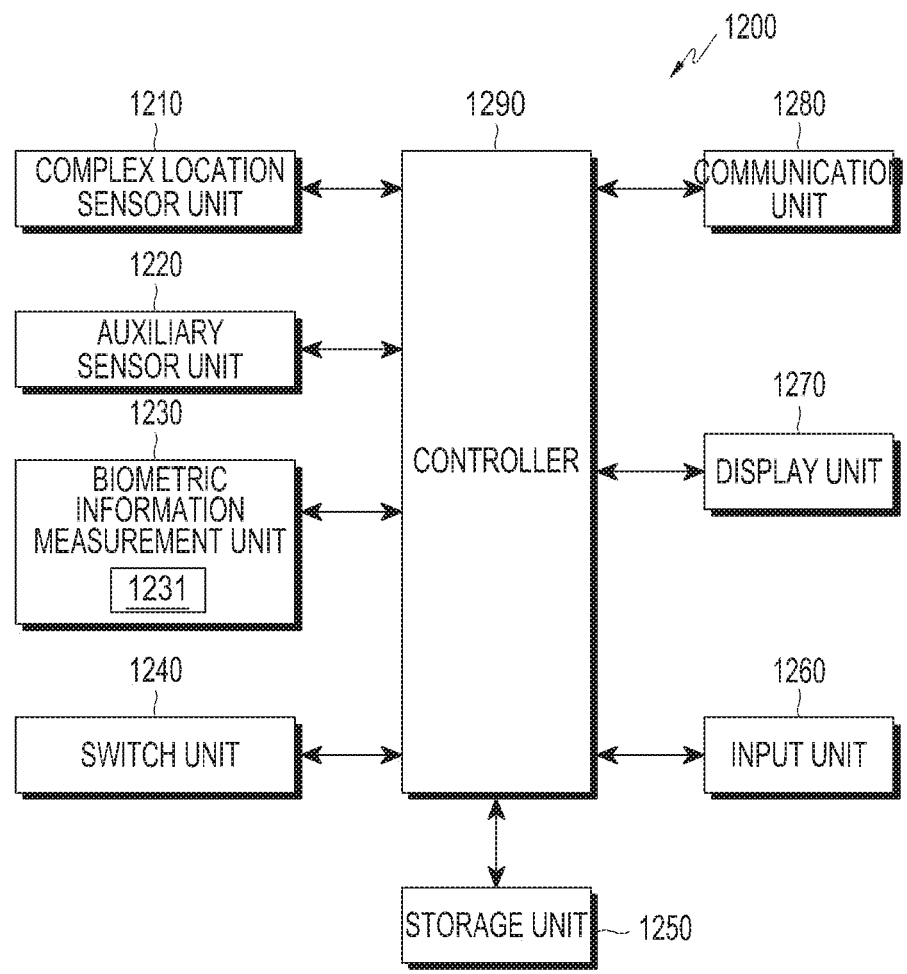
FIG. 12 is a block diagram schematically illustrating an electronic device for measuring biometric information according to various embodiments of the present disclosure.

FIG. 12 is a block diagram schematically illustrating an electronic device for measuring biometric information according to various embodiments of the present disclosure.

Referring to FIG. 12, an electronic device 1200 may include, for example, all or a part of the electronic device 101 illustrated in FIG. 1. The electronic device 1200 according to various embodiments of the present disclosure may include a complex location sensor unit 1210, an auxiliary sensor unit 1220 a biometric information measurement unit 1230, a switch unit 1240, and a controller 1290. Further, the electronic device 1200 may further include a storage unit 1250, an input unit 1260, a display unit 1270, and a communication unit 1280.

The complex location sensor unit 1210 may detect a plurality of pieces of location information (or a plurality of pieces of sensor information for calculating one piece of position (and/or location) information) in measurement points. The complex location sensor unit 1210 may include a plurality of location-based sensors and may detect each of the plurality of pieces of location information on the measurement point from the plurality of location-based sensors. According to an embodiment of the present disclosure, the plurality of pieces of location information may include an acceleration value, a geomagnetic value, and an altitude value. Further, the plurality of pieces of location information may include location-based detection values detected from all the location-based sensors, such as a gyro detection value, an angular speed detection value, and a motion detection value, but are not limited thereto. The controller 1290 may recognize a location and attitude of the electronic device 1200 in the measurement point based on the plurality of pieces of location information detected by the complex location sensor unit 1210 and determine an electrode array of a plurality of electrodes according to the recognized location and attitude of the electronic device 1200.

The electrode array includes locations, directions, polarities, and/or the arrangement of electrode channels of the plurality of electrodes. For example, the electrode array may include the location of each electrode and/or the polarity arrangement. The electrode array may include the arrangement of a current electrode channel to which the current is applied and/or a voltage electrode channel for measuring the voltage.

The auxiliary sensor unit 1220 may detect information on a plurality of auxiliary sensors subsidiarily used for determining a measurement pose of the examinee in the measurement point. The auxiliary sensor unit 1220 may include a plurality of auxiliary sensors for determining the measurement pose of the examinee and may detect each of a plurality of pieces of auxiliary sensor information on the measurement pose. For example, the auxiliary sensor unit 1220 may include a piezoelectric sensor, a proximity sensor, and a temperature sensor. Further, the plurality of pieces of auxiliary sensor information may include a strain gage value detected by the piezoelectric sensor, a proximity value detected by the proximity sensor, and a temperature value detected by the temperature sensor.

The biometric information measurement unit 1230 may detect biometric information of the examinee through a plurality of electrodes having an electrode array electrically connected thereto. The electrode array may include all of the arrangements of respective electrodes according to the location, direction, polarity, and electrode channel of the electrode. According to the present embodiment of the present disclosure, the biometric information measurement unit 1230 may detect biometric information (for example, body resistance) on the examinee from the plurality of electrodes controlled to have a preset electrode array according to the measurement pose of the examinee.

For example, the biometric information measurement unit 1230 may include a body resistance measurement module 1231. The body resistance measurement module 1231 may detect a size of the body resistance according to an amount of body fat of a measurement part which the examinee desires to measure. For example, the body resistance measurement module 1231 may detect two types of body resistance (for example, bio impedance and electrodermal activity (EDA) according to a measurement method.

The body resistance measurement module 1231 may detect an impedance value calculated by applying the alternate current passing through the measurement point through two electrodes which contact the measurement point and measuring a voltage at a time when the alternate current passes through the measurement point through two other electrodes which contact the measurement point. The impedance value may have different impedance standard ranges according to the measurement part and the measurement pose of the examinee. Accordingly, the controller 1290 may distinguish between measurement poses according to the impedance value detected by the body resistance measurement module 1231 and analyze a body composition of the examinee based on the detected impedance value.

The body resistance measurement module 1231 may detect a skin conductivity value calculated by applying the direct current passing through the measurement point through two electrodes which contact the measurement point and measuring a voltage at a time when the direct current passes through the measurement point through two other electrodes which contact the measurement point. For example, the skin conductivity refers to a measurement value of a temporary change of electric resistance detected by a weak electric signal direct current (DC) applied to the measurement point and may have different skin conductivity standard ranges according to the contact part, that is, the measurement part. The controller 1290 may distinguish between contact parts, that is, measurement parts according to the skin conductivity value detected by the body resistance measurement module 1231. A measurement pose specific-impedance range, a skin conductivity range, a direction of a reference axis of an acceleration sensor 1302, and an angle of a reference axis of a geomagnetic sensor 1304 are defined according to the measurement pose in Table 1 below.

Although the present disclosure divides the measurement pose of the examinee into four types for convenience of the description, the present disclosure is not limited thereto and the measurement pose may be more variously divided.

TABLE 1

|  | First measurement pose | Second measurement pose | Third measurement pose | Fourth measurement pose |
| --- | --- | --- | --- | --- |
| Impedance [Ω] | 510~850 | 530~870 | 600~10000 | 560~900 |
| Skin conductivity [Ω] | Within tens of meters | Within tens of meters | Within 10 M | Within 5 M |
| Acceleration sensor | +Z axis: down | +Z axis: up | +Y axis: up/down +X axis: up/down | +Z axis: up/down |
| Geomagnetic sensor | Z axis: 90° | Z axis: −90° | Z axis: 0°/180° | Z axis: 90°/−90° |

As shown in Table 1, it is noted that the measurement pose specific-impedance and the measurement pose specific-skin conductivity vary depending on the measurement pose and the direction of the reference axis of the acceleration sensor 1302 and the angle of the reference axis of the geomagnetic sensor 1304 vary depending on the measurement pose. Accordingly, the controller 1290 may recognize the location and the attitude of the electronic device 1200 according to the plurality of pieces of location information (or a plurality of pieces of sensor information for calculating one piece of attitude (and/or location) information) detected by the complex location sensor unit 1210 and distinguish between a plurality of preset measurement poses of the examinee, so as to determine the measurement pose. Further, the controller 1290 may distinguish between the preset measurement poses according to the impedance and the skin conductivity detected by the biometric information measurement unit 1230 and determine the measurement pose. For example, the controller 1290 may finally determine the measurement pose of the examinee by complexly using the plurality of pieces of detected location information and the plurality of pieces of detected biometric information (for example, body resistance, such as the impedance and the skin conductivity). In addition, the controller 1290 may determine the measurement pose of the examinee based on the plurality of pieces of detected auxiliary detection information. For example, the controller 1290 may determine a plurality of preset measurement poses by distinguishing between measurement parts (for example, thigh, palm, and finger) through the detected strain gage value.

The switch unit 1240 may include a plurality of switches (or one switch including at least one input port and at least one output port) corresponding to the plurality of electrodes, respectively, and may electrically connect the plurality of electrodes and the biometric information measurement unit 1230 through the plurality of switches. The switch unit 1240 may be controlled to change the electrode array connected between the plurality of electrodes and the biometric information measurement unit 1230 according to a control of the controller 1290. The controller 1290 may recognize the location and the attitude of the electronic device 1200 based on the plurality of pieces of detected location information and the plurality of pieces of auxiliary detection information, and determine the measurement pose according to the recognized location and attitude.

Figure 13:
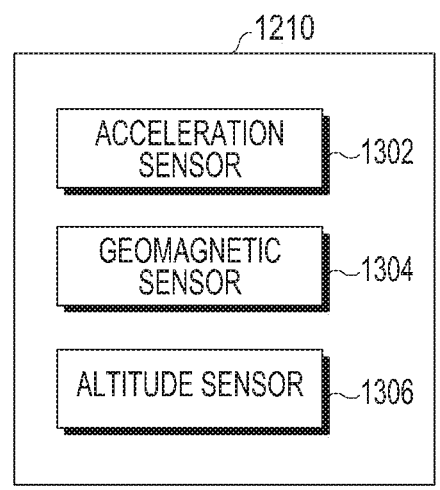
FIG. 13 is a block diagram illustrating a complex location sensor unit according to various embodiments of the present disclosure.
Figure 14A:
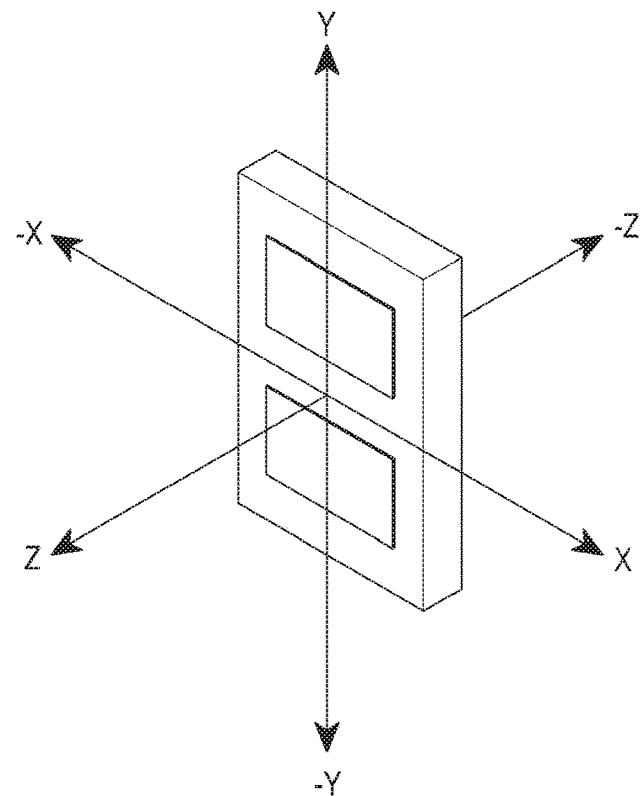
FIG. 14A is a perspective view illustrating a reference direction of an electronic device according to various embodiments of the present disclosure.
Figure 14B:
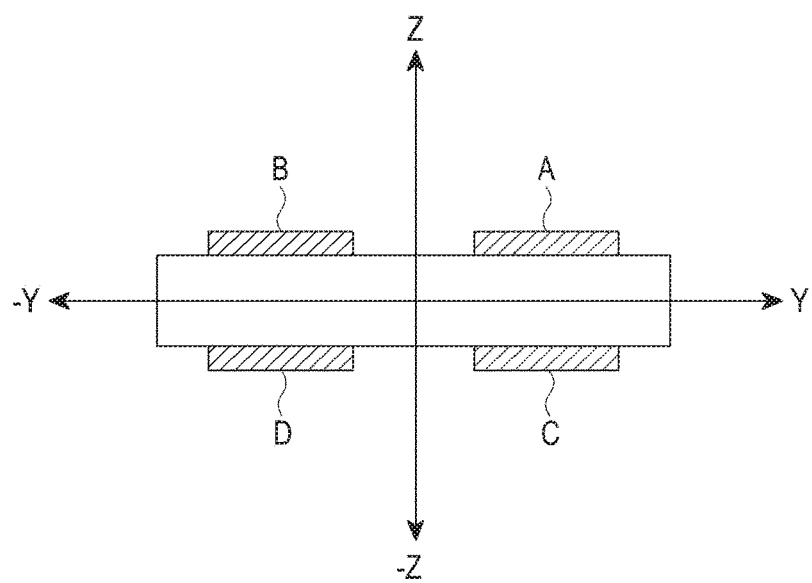
FIG. 14B is a cross-sectional view of FIG. 14A according to various embodiments of the present disclosure.

FIG. 13 is a block diagram illustrating a complex location sensor unit according to various embodiments of the present disclosure, FIG. 14A is a perspective view illustrating a reference direction of an electronic device according to various embodiments of the present disclosure, and FIG. 14B is a cross-sectional view of FIG. 14A according to various embodiments of the present disclosure.

Referring to FIGS. 13, 14A, and 14B, the complex location sensor unit 1210 may include an acceleration sensor 1302, a geomagnetic sensor 1304, and an altimeter sensor 1306.

The acceleration sensor 1302 may detect an acceleration value in a measurement point when the electronic device 1200 moves. According to the present disclosure, as illustrated in FIG. 14A, the acceleration sensor 1302 may have three axes including a Y axis corresponding to a major axis length direction of the electronic device 1200 based on the center of the electronic device 1200, an X axis corresponding to a minor axis length direction of the electronic device 1200, and a Z axis corresponding to a direction orthogonal to the plane (for example, the front surface) with the X axis and the Y axis, and it is assumed that directions of the X axis, the Y axis, and the Z axis of the electronic device 1200 are set as reference directions in a state where the Y axis is orthogonal to the horizontal plane, and the X axis and the Z axis are parallel to the horizontal plane. For example, the acceleration sensor 1302 may have reference directions including an upward direction from the center of the electronic device 1200, which is a +Y axis (a direction opposite thereto is a −Y axis), a rightward direction from the center of the electronic device 1200, which is a +X (a direction opposite thereto is an −X axis), and a forward direction from the center of the electronic device 1200, which is a +Z axis (a direction opposite thereto is a −Z axis).

The geomagnetic sensor 1304 may detect a direction angle of the electronic device 1200 by Earth's magnetic field in a measurement point where the electronic device 1200 is located. According to the present disclosure, the geomagnetic sensor 1304 may have reference angles having rotation angles (that is, direction angles) (for example, a pitch angle, a roll angle, and a yaw angle) of 0 degrees with respect to the X axis, the Y axis, and the Z axis of the electronic device 200 in a state where the geomagnetic sensor 1304 has three axes equal to those of the acceleration sensor 302, and the Y axis is orthogonal to the horizontal plane and the X and Z axes are parallel to the horizontal plane as illustrated in FIG. 14A. The controller 1290 may recognize an attitude angle of the electronic device 1200 through the geomagnetic value detected by the geomagnetic sensor 1304.

The altimeter sensor 1306 may detect an altitude (height) of the electronic device 1200 by an air pressure at a measurement point where the electronic device 1200 is located.

In the present embodiment of the present disclosure, the location and the attitude of the electronic device 1200 are determined according to a measurement pose of the examinee, and the electrode array (for example, arrangement of the current electrode channel and the voltage electrode channel) may be controlled to be a preset measurement pose-specific electrode array based on the determined measurement pose. For example, the electronic device 1200 for measuring biometric information according to various embodiments of the present disclosure may have two electrodes (for example, electrode A and electrode B) formed on the front surface and two electrodes (for example, electrode C and electrode D) formed on the rear surface as illustrated in FIGS. 14A and 14B. The electrodes A, B, C, and D may control the electrode array of current electrode channels for applying the current and voltage electrode channel for detecting the voltage according to the measurement pose of the examinee. In the present embodiment of the present disclosure, although the electronic device 1200 based on 4 electrodes is illustrated, the present disclosure is not limited thereto and may include more channel electrodes.

The storage unit 1250 may store in advance electrode array information on each electrode and basic information of the examinee. The electrode array information may include the location, direction, polarity, and arrangement of the electrode channel of each electrode. The basic information may include the name, age, gender, height, and weight of the examinee. Further, the storage unit 1250 may store in advance the impedance standard range and the skin conductivity standard range according to each of a plurality of measurement poses based on the age, gender, and height of the examinee.

The input unit 1260 may receive various input signals generated or input by the user or examinee. According to an embodiment of the present disclosure, the input unit 1260 may include a key pad, a touch pad, and a voice input module, such as a microphone. Further, the input unit 1260 is not limited thereto and may include all input means which can make an input into the electronic device 1200 according to various embodiments of the present disclosure.

The display unit 1270 may display, on the screen, a health state analysis result analyzed based on the biometric information detected by the biometric information measurement unit 1230 through the electrode array of the plurality of electrodes controlled by the controller 1290. For example, the health state analysis result may include a body composition result analyzed based on the body resistance detected by the biometric information measurement unit 1230. According to an embodiment of the present disclosure, when the detected biometric information corresponds to a body resistance value, the display unit 1270 may display a body composition analysis result, such as total body water, muscle mass, total weight without fat, balance of right and left, balance of top and bottom, and an obesity level, analyzed based on the impedance and the skin conductivity.

The communication unit 1280 may receive information required for measuring the biometric information according to the present disclosure from the outside. For example, the communication unit 1280 may receive an average body mass index (BMI), a measurement pose-specific impedance standard range, and a measurement pose-specific skin conductivity standard range according to the age, gender, and height of the examinee from the outside (for example, the server 106).

The controller 1290 may overall control the electronic device 1200 according to various embodiments of the present disclosure. The controller 1290 may recognize the location and the attitude of the electronic device 1200 based on the plurality of pieces of location information detected through the complex location sensor unit 1210 and determine the measurement pose of the examinee based on the recognized location and attitude and the plurality of pieces of auxiliary detection information detected by the auxiliary sensor unit 1220. The controller 1290 may control the switch unit 1240 to connect the preset electrode array according to the determined measurement pose to the biometric information measurement unit 1230. When determining the measurement pose of the examinee, the controller 1290 may more precisely determine the measurement pose of the examinee based on the plurality of pieces of auxiliary detection information including a strain gage value, a proximity value, and a temperature value detected through the auxiliary sensor unit 1220. The controller 1290 may analyze a health state of the examinee through a body composition result analyzed using the plurality of pieces of biometric information (for example, body resistance) detected through the preset electrode array according to the determined measurement pose. Further, the controller 1290 may correct an error of the determined measurement pose based on a measurement pose-specific reference biometric information range (for example, impedance range) according to the age, gender, and height of the examinee stored in advance in the storage unit 1250. The controller 1290 may analyze the health state of the examinee through the body composition result analyzed using biometric information (for example, impedance) re-detected by the biometric information measurement unit 1230 through the plurality of electrodes controlled to have a preset electrode array according to the corrected measurement pose.

Figure 15:
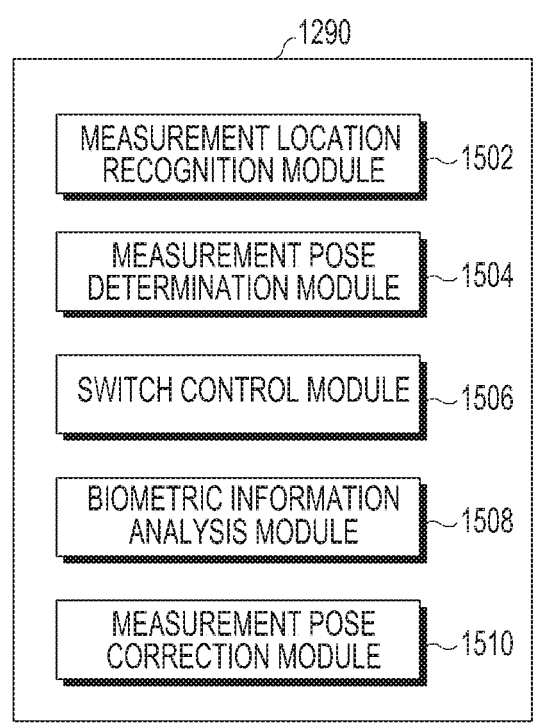
FIG. 15 is a block diagram illustrating a controller according to various embodiments of the present disclosure.

FIG. 15 is a block diagram illustrating a controller according to various embodiments of the present disclosure.

Referring to FIG. 15, the controller 1290 may include a measurement location recognition module 1502, a measurement pose determination module 1504, a switch control module 1506, a biometric information analysis module 1508, and a measurement pose correction module 1510.

The measurement location recognition module 1502 may recognize a location and an attitude of the electronic device 1200 based on a plurality of pieces of location information detected in a measurement point. The measurement location recognition module 1502 may calculate a direction and an angle of each axis changed from a reference direction and a reference angle of each axis of the complex location sensor unit 1210 by using an acceleration value and a geomagnetic value detected in the measurement point and recognize the location and the attitude of the electronic device 1200 based on the location information including an altitude according to the altitude value detected in the measurement point.

The measurement pose determination module 1504 may distinguish between a plurality of preset measurement poses based on the location and the attitude of the electronic device 1200 recognized by the measurement location recognition module 1502, biometric information (for example, body resistance including an impedance value and a skin conductivity value) detected by the biometric information measurement unit 1230, and the plurality of pieces of auxiliary detection information (for example, the strain gage value, the proximity value, and the temperature value in the measurement point) detected by the auxiliary sensor unit 1220 and determine the measurement pose of the examinee.

The measurement pose determination module 1504 may select the measurement pose complexly corresponding to the recognized location and attitude of the electronic device 1200, and the detected impedance value, skin conductivity value, strain gage value, proximity value, and temperature value within a preset measurement pose-specific location and attitude range of the electronic device 1200, an impedance range, a skin conductivity range, a strain gage range, a proximity range, and a temperature range, and determine the selected measurement pose as the measurement pose of the examinee.

The switch control module 1506 may control the switch unit 1240 to change the electrode array of the plurality of electrodes into the electrode array corresponding to the measurement pose determined by the measurement pose determination module 1504 among preset electrode arrays according to the measurement pose. For example, the electrode array may include the arrangement of current electrode channels for applying the current to the corresponding measurement part according to the preset measurement pose and voltage electrode channels for detecting the voltage from the corresponding measurement part.

The biometric information analysis module 1508 may analyze health state information of the examinee by analyzing the biometric information detected by the biometric information measurement unit 1230 through the plurality of electrodes. For example, the biometric information may include body resistance including the impedance and the skin conductivity. The health state information may include a body composition analyzed based on the detected body resistance.

The measurement pose correction module 1510 may correct the measurement pose detected by the measurement pose determination module 1504 in accordance with a biometric information difference between the detected biometric information and preset measurement pose-specific reference biometric information. In this case, the controller 1290 may switch the corresponding switch of each electrode to control the electrode array to be an electrode array corresponding to the corrected measurement pose among the preset measurement pose-specific electrode arrays. Further, the controller 1290 may re-detect the biometric information (for example, body resistance) by the biometric information measurement unit 1230 through the plurality of electrodes of the controlled electrode array. The controller 1290 may analyze the health state information (for example, body composition) based on the biometric information re-detected through the biometric information analysis module 1508.

Figure 16A:
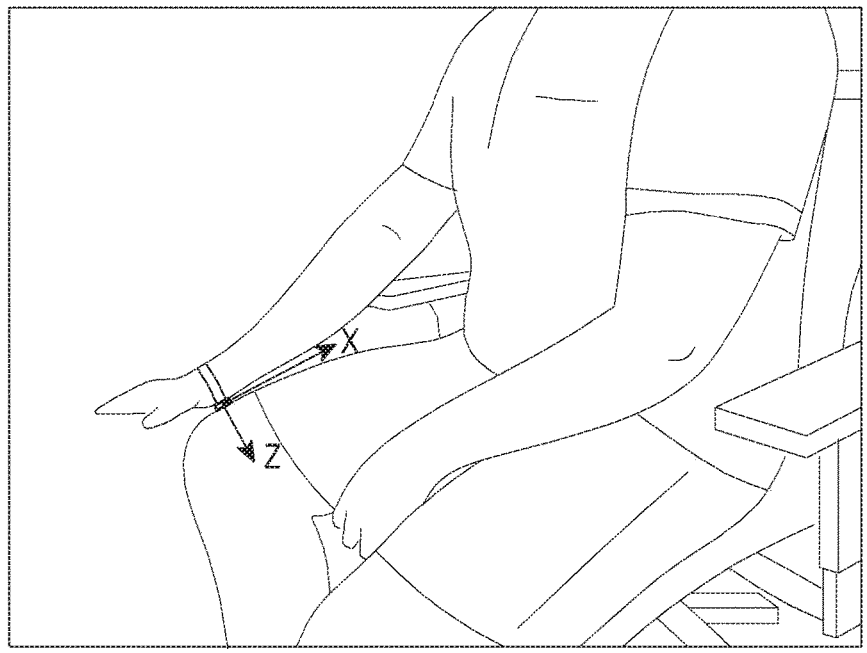
FIG. 16A illustrates a measurement pose when biometric information is measured according to various embodiments of the present disclosure.
Figure 16B:
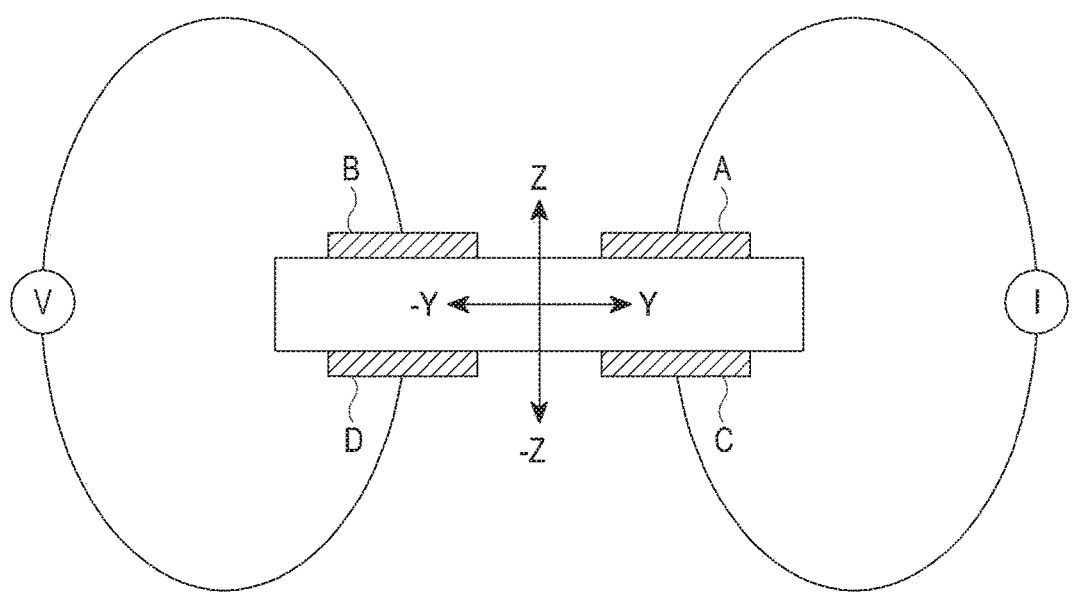
FIG. 16B illustrates an electrode array according to a measurement pose illustrated in FIG. 16A according to various embodiments of the present disclosure.

FIG. 16A illustrates a measurement pose when biometric information is measured according to various embodiments of the present disclosure, and FIG. 16B illustrates an electrode array according to a measurement pose illustrated in FIG. 16A according to various embodiments of the present disclosure.

Referring to FIGS. 16A and 16B, a pose (hereinafter, referred to as a "first measurement pose") in which the examinee brings the electronic device 1200 worn on the wrist into contact with the thigh in a state where the examinee sits on a chair is illustrated. In the first measurement pose, body resistance may be measured over a right arm (RA)-torso (TR)-right leg (RL). The first measurement pose may have an electrode array as illustrated in FIG. 16B. For example, in the first measurement pose, the electronic device 1200 may be recognized to have an attitude in which the Z axis of the acceleration sensor 1302 faces downward and the Z axis of the geomagnetic sensor 1304 is located at 90 degrees. For example, when the measurement pose of the examinee is determined as the first measurement pose by the measurement pose determination module 1504 of the controller 1290, the switch control module 1506 of the controller 1290 may control the switch unit 1240 to arrange the electrode A formed on the front surface of the electronic device 1200 and the electrode C formed on the rear surface of the electronic device 1200 as the current channel electrodes and the electrode B formed on the front surface of the electronic device 1200 and the electrode D formed on the rear surface of the electronic device 1200 as the voltage channel electrodes.

Figure 17A:
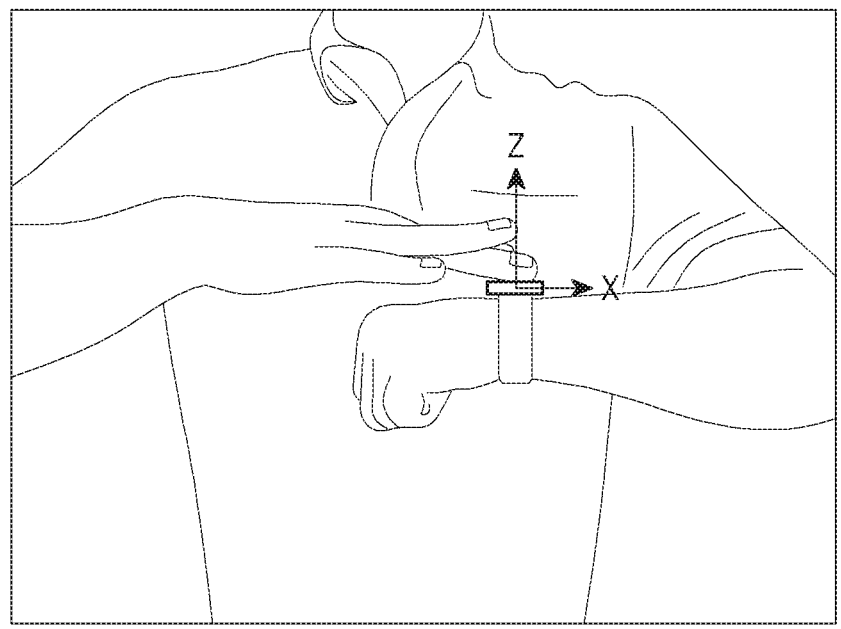
FIG. 17A illustrates a measurement pose when biometric information is measured according to various embodiments of the present disclosure.
Figure 17B:
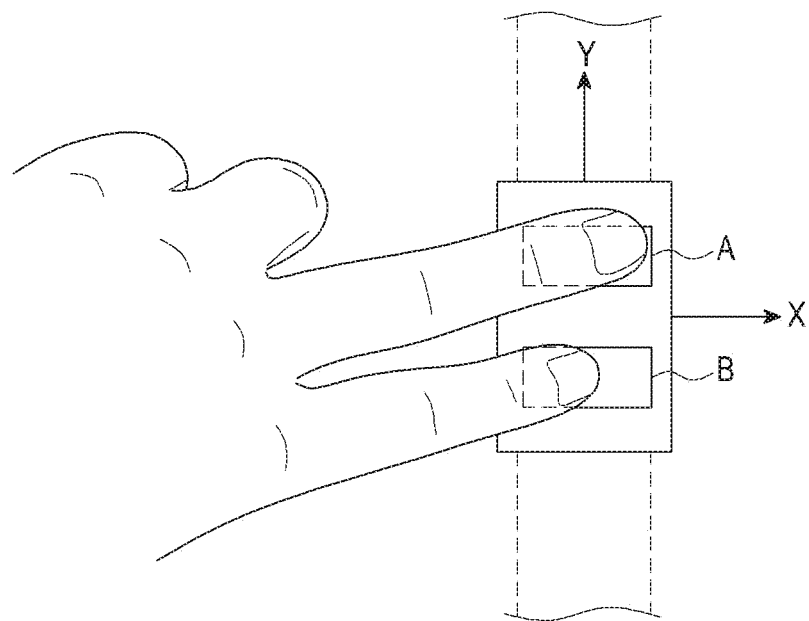
FIG. 17B is a top view of FIG. 17A according to various embodiments of the present disclosure.
Figure 17C:
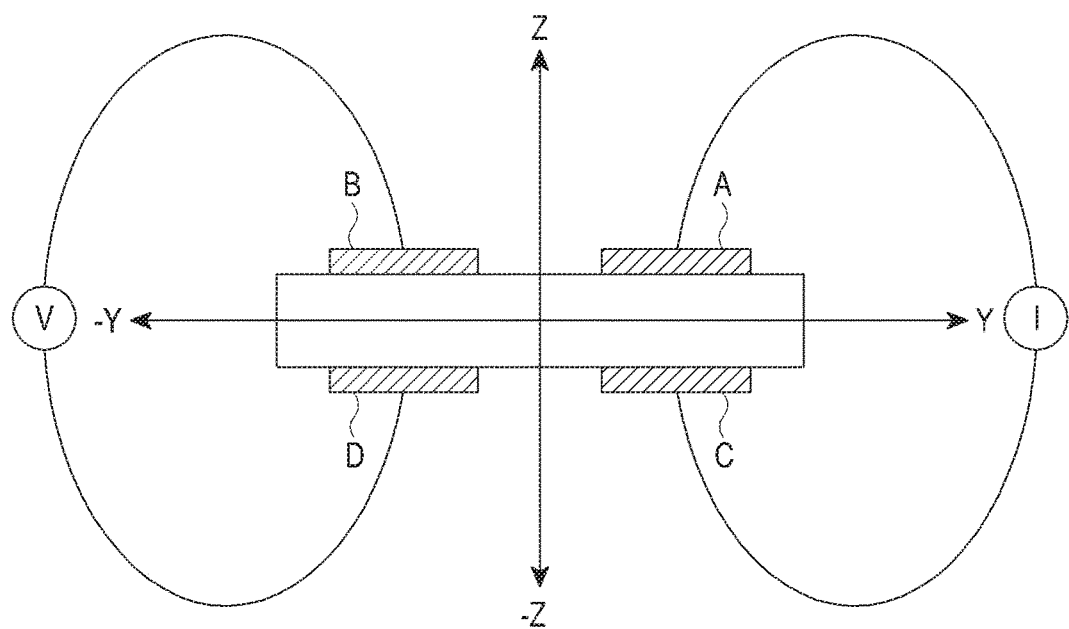
FIG. 17C illustrates an electrode array according to the measurement pose illustrated in FIG. 17A according to various embodiments of the present disclosure.

FIG. 17A illustrates a measurement pose when biometric information is measured according to various embodiments of the present disclosure, and FIG. 17B is a top view of FIG. 17A according to various embodiments of the present disclosure, and FIG. 17C illustrates an electrode array according to the measurement pose illustrated in FIG. 17A according to various embodiments of the present disclosure.

Referring to FIGS. 17A, 17B, and 17C, a pose (hereinafter, referred to as a "second measurement pose") in which the examinee brings fingers of one hand into contact with electrodes (for example, electrode A and electrode B) formed on the top surface of the electronic device 1200 worn on the other hand is illustrated. In the second measurement pose, body resistance may be measured over a bent RA-left arm (LA). The second measurement pose may have an electrode array as illustrated in FIG. 17C. For example, in the second measurement pose, the electronic device 1200 may be recognized to have an attitude in which the Z axis of the acceleration sensor 1302 faces upward and the Z axis of the geomagnetic sensor 1304 is located at −90 degrees. For example, when the measurement pose of the examinee is determined as the second measurement pose by the measurement pose determination module 1504 of the controller 1290, the switch control module 1506 of the controller 1290 may control the switch unit 1240 to arrange the electrode A formed on the front surface of the electronic device 1200 and the electrode C formed on the rear surface of the electronic device 1200 as the current channel electrodes and the electrode B formed on the front surface of the electronic device 1200 and the electrode D formed on the rear surface of the electronic device 1200 as the voltage channel electrodes.

Figure 18A:
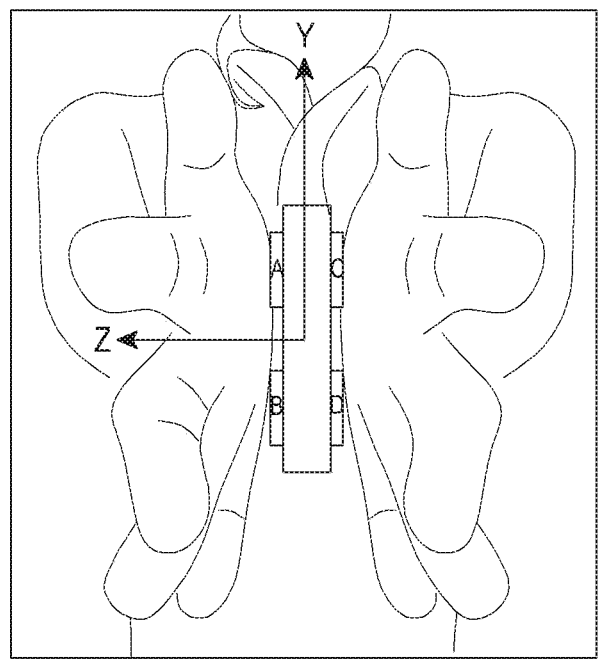
FIG. 18A illustrates a measurement pose when biometric information is measured according to various embodiments of the present disclosure.
Figure 18B:
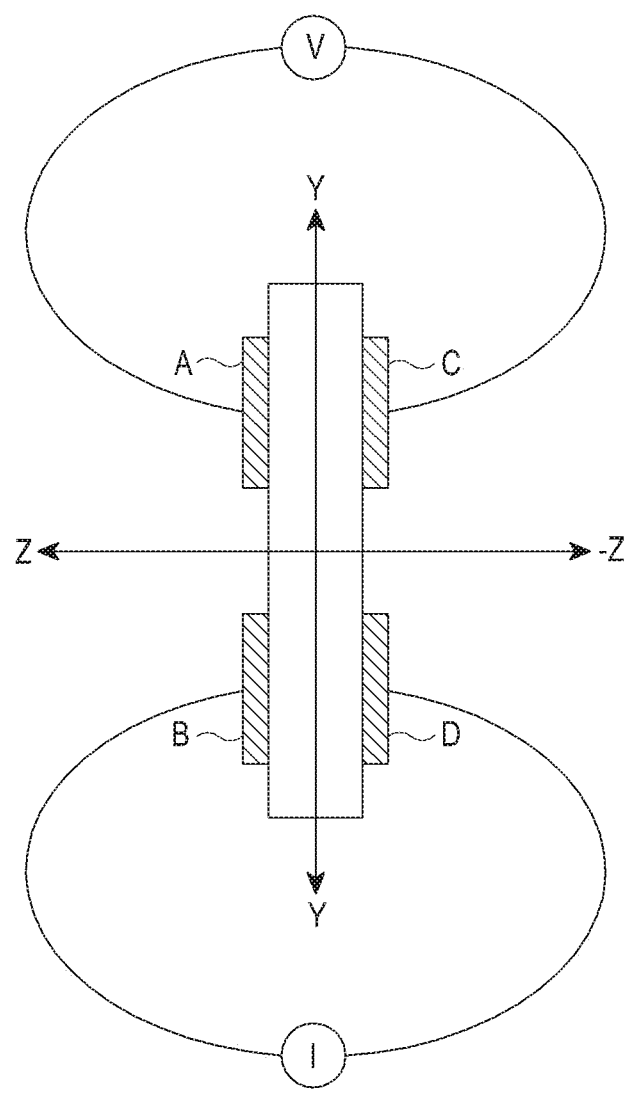
FIG. 18B illustrates an electrode array according to a measurement pose illustrated in FIG. 18A according to various embodiments of the present disclosure.

FIG. 18A illustrates a measurement pose when biometric information is measured according to various embodiments of the present disclosure, and FIG. 18B illustrates an electrode array according to the measurement pose illustrated in FIG. 18A according to various embodiments of the present disclosure.

Referring to FIGS. 18A and 18B, a pose (hereinafter, referred to as a "third measurement pose") in which the examinee presses electrodes of the electronic device 1200 with both palms in a state wherein the examinee stretches forth both arms is illustrated. In the third measurement pose, body resistance may be measured over a straightened RA-LA. The third measurement pose may have an electrode array as illustrated in FIG. 18B. For example, in the third measurement pose, the electronic device 1200 may be recognized to have an attitude in which the +Z axis of the acceleration sensor 1302 faces upward or downward or the +Y axis faces upward or downward and the Z axis of the geomagnetic sensor 1304 is located at 0 degrees or −180 degrees. For example, when the measurement pose of the examinee is determined as the third measurement pose by the measurement pose determination module 1504 of the controller 1290, the switch control module 1506 of the controller 1290 may control the switch unit 1240 to arrange the electrode A formed on the front surface of the electronic device 1200 and the electrode C formed on the rear surface of the electronic device 1200 as the voltage channel electrodes and the electrode B formed on the front surface of the electronic device 1200 and the electrode D formed on the rear surface of the electronic device 1200 as the current channel electrodes.

Figure 19A:
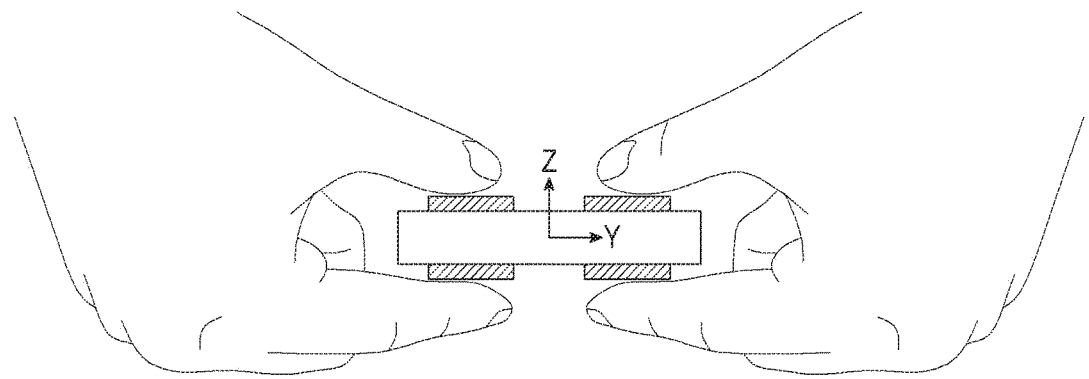
FIG. 19A illustrates a measurement pose when biometric information is measured according to various embodiments of the present disclosure.
Figure 19B:
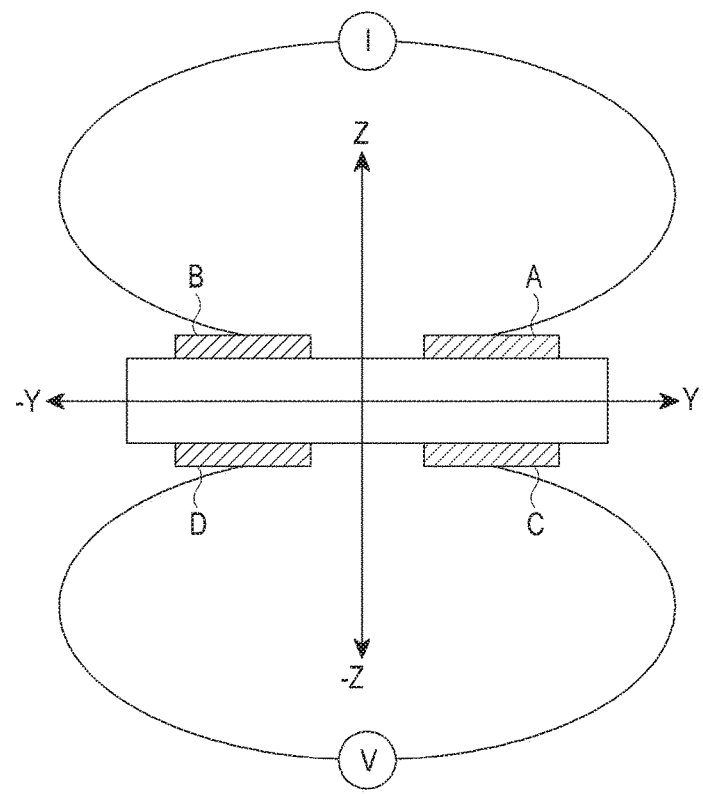
FIG. 19B illustrates an electrode array according to an measurement pose illustrated in FIG. 19A according to various embodiments of the present disclosure.

FIG. 19A illustrates a measurement pose when biometric information is measured according to various embodiments of the present disclosure, and FIG. 19B illustrates an electrode array according to a measurement pose illustrated in FIG. 19A according to various embodiments of the present disclosure.

Referring to FIGS. 19A and 19B, a pose (hereinafter, referred to as a "fourth measurement pose") in which the examinee pinches electrodes of the electronic device 1200 with fingers of both hands in a state wherein the examinee stretches forth both arms is illustrated. In the fourth measurement pose, body resistance may be measured over a straightened RA-LA. The fourth measurement pose may have an electrode array as illustrated in FIG. 19B. For example, in the fourth measurement pose, the electronic device 1200 may be recognized to have an attitude in which the +Z axis of the acceleration sensor 1302 faces upward or downward and the Z axis of the geomagnetic sensor 1304 is located at 90 degrees or −90 degrees. For example, when the measurement pose of the examinee is determined as the fourth measurement pose by the measurement pose determination module 1504 of the controller 1290, the switch control module 1506 of the controller 1290 may control the switch unit 1240 to arrange the electrodes A and B formed on the front surface of the electronic device 1200 as the current channel electrodes and the electrodes C and D formed on the rear surface of the electronic device 1200 as the voltage channel electrodes.

As illustrated in FIGS. 16A, 16B, 17A, 17B, 17C, 18A, 18B, 19A, and 19B, the electrodes (electrodes A, B, C, and D) of the electronic device 1200 may have different electrode arrays (current channel electrodes and voltage channel electrodes) according to the measurement pose of the examinee.

According to an embodiment of the present disclosure, an electronic device for measuring biometric information may include a complex location sensor unit configured to detect a plurality of pieces of location information in a measurement point, an auxiliary sensor unit configured to detect a plurality of pieces of auxiliary detection information in the measurement point, a biometric information measurement unit configured to detect biometric information through a plurality of electrodes formed on at least one surface of the electronic device, a switch unit electrically connected to the biometric information measurement unit and including a plurality of switches (or one switch including at least one input port and at least one output port) corresponding to the plurality of electrodes, respectively, and a controller configured to determine a measurement pose of the examinee according to an attitude of the electronic device in the measurement point based on the plurality of pieces of detected location information and the plurality of pieces of detected auxiliary detection information and control the switch unit to change an electrode array of the plurality of electrodes into an electrode array corresponding to the determined measurement pose among preset measurement pose-specific electrode arrays.

According to an embodiment of the present disclosure, the complex location sensor unit may include an acceleration sensor configured to detect an acceleration value in the measurement point, a geomagnetic sensor configured to detect a geomagnetic value in the measurement point, and an altitude sensor configured to detect an altitude value in the measurement point.

According to an embodiment of the present disclosure, the auxiliary sensor unit may include a piezoelectric sensor configured to detect a strain gage value in the measurement point, a proximity sensor configured to detect a proximity value in the measurement point, and a temperature sensor configured to detect a temperature value in the measurement point.

According to an embodiment of the present disclosure, the biometric information measurement unit may include a body resistance measurement module configured to detect body resistance of the examinee.

According to an embodiment of the present disclosure, the body resistance measurement module may detect impedance and skin conductivity according to the determined measurement pose.

According to an embodiment of the present disclosure, the controller may include a measurement location recognition module configured to recognize a location and an attitude of the electronic device in the measurement point by using the plurality of pieces of detected location information, a measurement pose determination module configured to determine the measurement pose of the examinee by using the recognized location and attitude of the electronic device, and the detected body resistance value and the plurality of pieces of auxiliary detection information, and a switch control module configured to control the switch unit to change the array of the plurality of electrodes into the electrode array corresponding to the determined measurement pose among the preset measurement pose-specific electrode arrays.

According to an embodiment of the present disclosure, the measurement location recognition module may calculate a direction and an angle of each axis changed from a reference direction and a reference angle of each axis of the complex location sensor unit by using the detected acceleration value and geomagnetic value and recognize the location and the attitude of the electronic device based on the calculated direction and angle of each axis and the detected altitude value.

According to an embodiment of the present disclosure, the measurement pose determination module may select a measurement pose corresponding to the recognized location and attitude of the electronic device, and the detected impedance value, skin conductivity value, strain gage value, proximity value, and temperature value within a preset measurement pose-specific location and attitude range of the electronic device, an impedance range, a skin conductivity range, a strain gage range, a proximity range, and a temperature range, and determine the selected measurement pose as the measurement pose of the examinee.

According to an embodiment of the present disclosure, the switch control module may switch a corresponding switch of each electrode to change the array of the plurality of electrodes into an electrode array corresponding to the determined measurement pose among the preset measurement pose-specific electrode arrays.

According to an embodiment of the present disclosure, the electrode array may include an arrangement of current electrode channels for applying the current to a corresponding measurement part according to a preset measurement pose and voltage electrode channels for detecting the voltage from the corresponding measurement part.

According to an embodiment of the present disclosure, the controller may further include a biometric information analysis module configured to analyze health state information of the examinee by analyzing the biometric information detected through the plurality of electrodes.

According to an embodiment of the present disclosure, the biometric information analysis module may analyze a body composition of the examinee based on body resistance detected through the plurality of electrodes of the controlled electrode array according to the determined measurement pose.

According to an embodiment of the present disclosure, the controller may further include a measurement pose correction module configured to correct the determined measurement pose in accordance with a biometric information difference between the detected biometric information and preset measurement pose-specific reference biometric information.

According to an embodiment of the present disclosure, the biometric information analysis module may analyze a body composition of the examinee based on body resistance re-detected through the controlled electrode array according to the corrected measurement pose.

Figure 20:
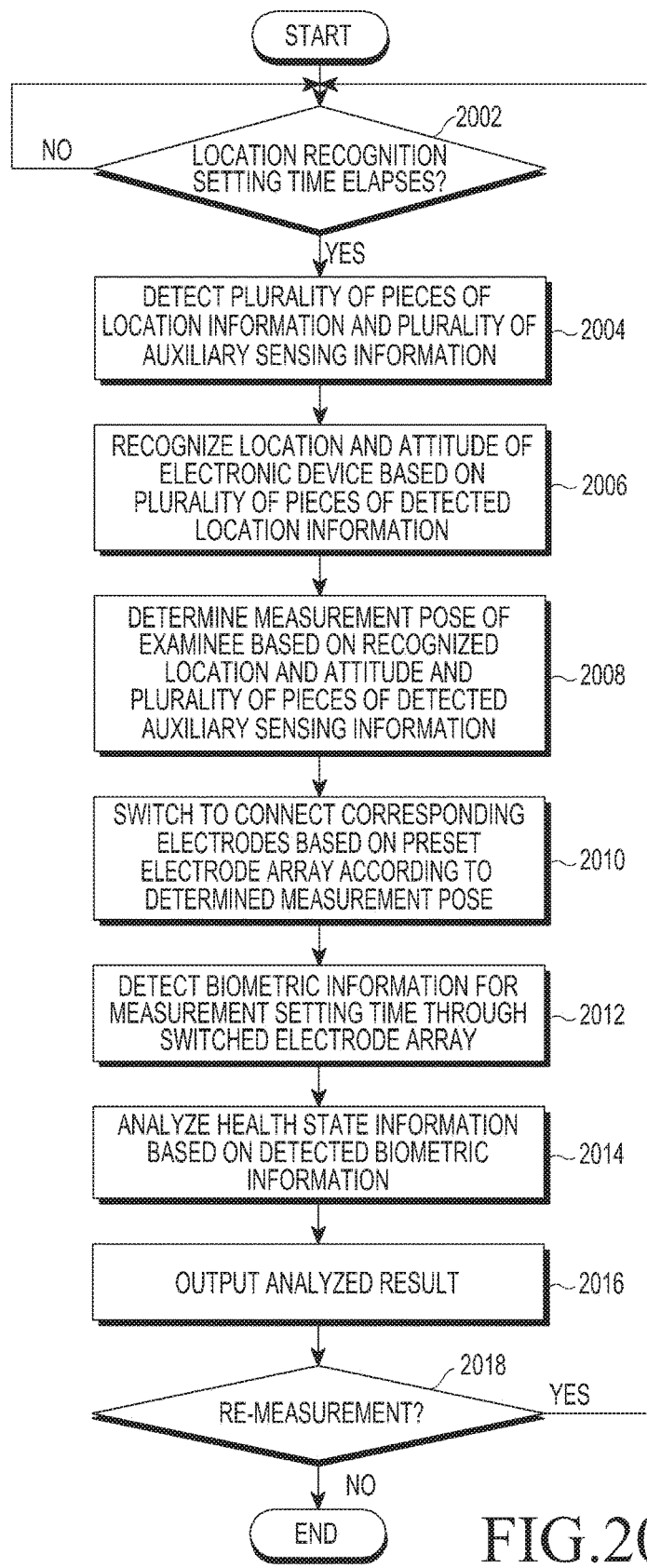
FIG. 20 is a flowchart illustrating a method of measuring biometric information according to various embodiments of the present disclosure.

FIG. 20 is a flowchart illustrating a method of measuring biometric information according to various embodiments of the present disclosure. In FIG. 20, a method of measuring biometric information (for example, impedance) through a change in an electrode array is described according to various embodiments of the present disclosure.

Referring to FIG. 20, the measurement location recognition module 1502 of the controller 1290 may determine whether a location recognition setting time (for example, 3 seconds) elapses in operation 2002. When the location recognition setting time elapses, the measurement location recognition module 1502 may detect a plurality of pieces of location information (for example, an acceleration value, a geomagnetic value, and an altitude value) through the complex location sensor unit 1210 of the electronic device 1200 in a corresponding measurement pose and detect a plurality of pieces of auxiliary detection information (for example, a strain gage value, a proximity value, and a temperature value) through the auxiliary sensor unit 1220 in operation 2004. When the location recognition setting time does not elapse in operation 2002, the measurement location recognition module 1502 returns to operation 2002 and repeats the following operations.

The controller 1290 may recognize a location and an attitude of the electronic device 1200 based on the plurality of pieces of location information detected through the measurement location recognition module 1502 in operations 2006. For example, the measurement location recognition module 1502 may calculate a direction and an angle of each axis changed from a reference direction and a reference angle of each axis of the complex location sensor unit 1210 by using the acceleration value and the geomagnetic value detected in the measurement point and recognize the location and the attitude of the electronic device 1200 based on the location information including an altitude according to the altitude value detected in the measurement point.

The controller 1290 may determine a measurement pose of the examinee based on the attitude recognized through the measurement pose determination module 1504 and the plurality of pieces of detected auxiliary detection information in operation 2008. For example, the measurement pose determination module 1504 may select the measurement pose complexly corresponding to the recognized location and attitude of the electronic device 1200, and the detected strain gage value, proximity value, and temperature value within a preset measurement pose-specific location and attitude range of the electronic device 1200, a strain gage range, a proximity range, and a temperature range, and determine the selected measurement pose as the measurement pose of the examinee.

The controller 1290 may switch, through the switch control module 1506, corresponding switches of the plurality of electrodes by controlling the switch unit 1240 to connect the changed electrode array, which corresponds to the determined measurement pose, among the preset measurement pose-specific electrode arrays in operation 2010.

The controller 1290 may detect biometric information from the biometric information measurement unit 1230 for a measurement setting time through the controlled electrode array through the biometric information analysis module 1508 in operation 2012, and analyze health state information based on the detected biometric information in operation 2014. For example, the biometric information may include body resistance including the impedance and the skin conductivity. Further, the health state information may include total body water (l), muscle mass (kg) of the whole body, an amount of body fat (kg), a total weight without fat (kg), a BMI, and an abdominal obesity level, analyzed based on the impedance.

The controller 1290 may output a result (for example, body composition) analyzed by the biometric information analysis module 1508 on the screen of the display unit 1270 in operation 2016.

Thereafter, the controller 1290 may determine whether a re-measuring signal for measuring the biometric information again is input in operation 2018. When the re-measuring signal is input, the controller 1290 may return to operation 2002 and repeat the following operations. When a re-measuring end signal is input in operation 2018, the controller 1290 may end the measurement of the biometric information.

Figure 21:
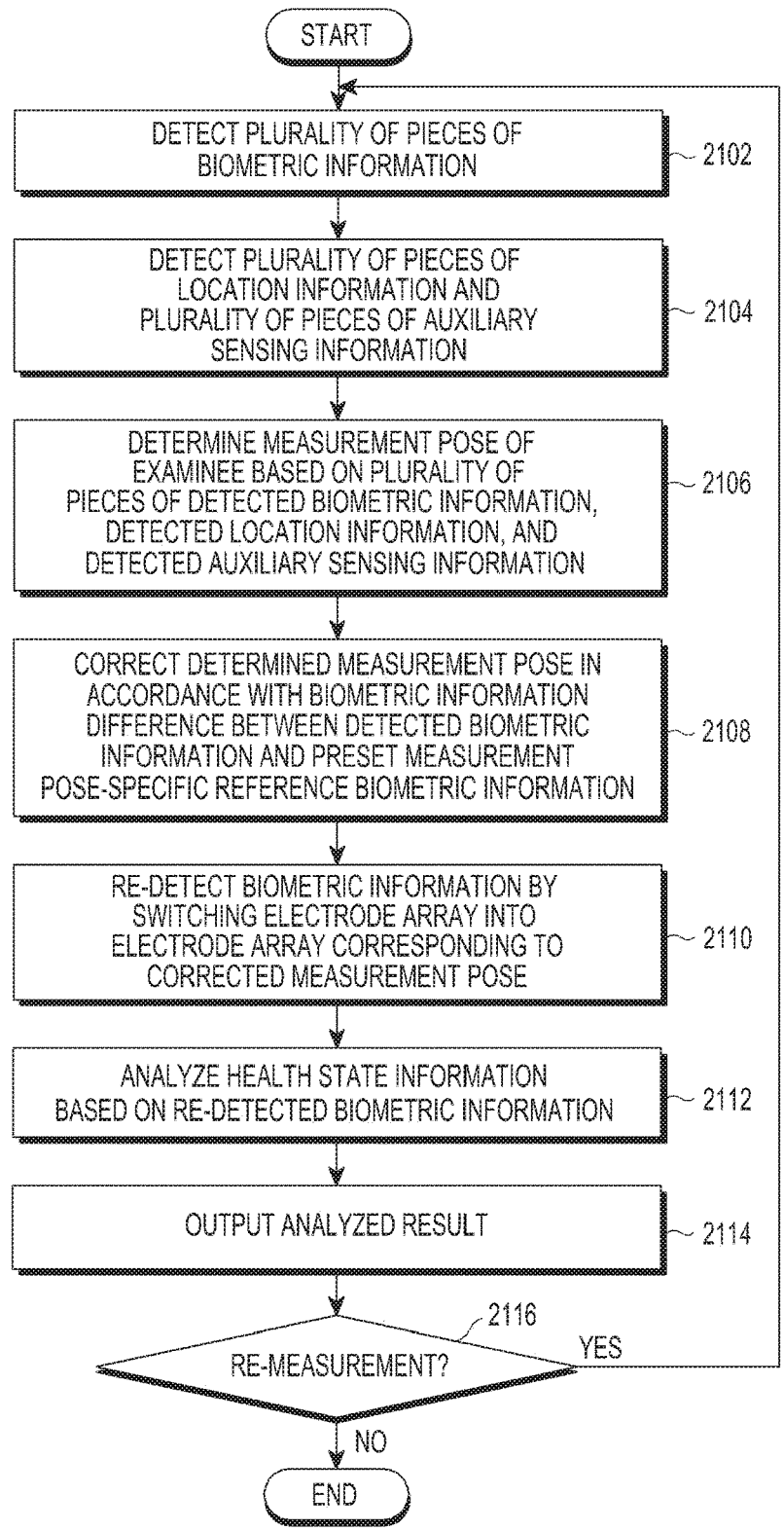
FIG. 21 is a flowchart illustrating a method of measuring biometric information according to various embodiments of the present disclosure.

FIG. 21 is a flowchart illustrating a method of measuring biometric information according to various embodiments of the present disclosure. In FIG. 21, a method of measuring biometric information through measurement pose correction is described according to various embodiments of the present disclosure.

Referring to FIG. 21, the controller 1290 detects a plurality of pieces biometric information through the biometric information measurement unit 1230 for a measurement setting time in operation 2102. For example, the plurality of pieces of biometric information may include the impedance and the skin conductivity.

The controller 1290 detects a plurality of pieces of location information (for example, an acceleration value, a geomagnetic value, and an altitude value) through the complex location sensor unit 1210 and detect a plurality of pieces of auxiliary detection information (for example, a strain gage value, a proximity value, and a temperature value) through the auxiliary sensor unit 1220 in operation 2104.

The controller 1290 may determine a measurement pose of the examinee based on the plurality of pieces of biometric information, the plurality of pieces of location information, and the plurality of pieces of auxiliary detection information detected through the measurement pose determination module 1504 in operation 2106. For example, the measurement pose determination module 1504 may select the measurement pose complexly corresponding to the recognized location and attitude of the electronic device 1200, and the detected impedance value, skin conductivity value, strain gage value, proximity value, and temperature value within a preset measurement pose-specific location and attitude range of the electronic device 1200, an impedance range, a skin conductive range, a strain gage range, a proximity range, and a temperature range, and determine the selected measurement pose as the measurement pose of the examinee.

The controller 1290 may correct the measurement pose determined in operation 2106 to compensate for a biometric information difference between the detected biometric information and preset measurement pose-specific reference biometric information through the measurement pose correction module 1510 in operation 2108.

The controller 1290 may re-detect, through the switch control module 1506, biometric information from the biometric information measurement unit 1230 by controlling the switch unit 1240 to change the electrode array to the electrode array corresponding to the corrected measurement pose, among the preset measurement pose-specific electrode arrays in operation 2110.

The controller 1290 may analyze the health state information based on the biometric information re-detected through the biometric information analysis module 1508 in operation 2112. For example, the biometric information may include body resistance including the impedance and the skin conductivity. Further, the health state information may include total body water (l), muscle mass (kg) of the whole body, an amount of body fat (kg), a total weight without fat (kg), a BMI, and an abdominal obesity level, analyzed based on the impedance.

The controller 1290 may output a result (for example, body composition) analyzed by the biometric information analysis module 1508 on the screen of the display unit 1270 in operation 2114.

Thereafter, the controller 1290 may determine whether a re-measuring signal for measuring the biometric information again is input in operation 2116. When the re-measuring signal is input, the controller 1290 may return to operation 2002 and repeat the following operations. When a re-measuring end signal is input in operation 2116, the controller 1290 may end the measurement of the biometric information.

Figure 22:
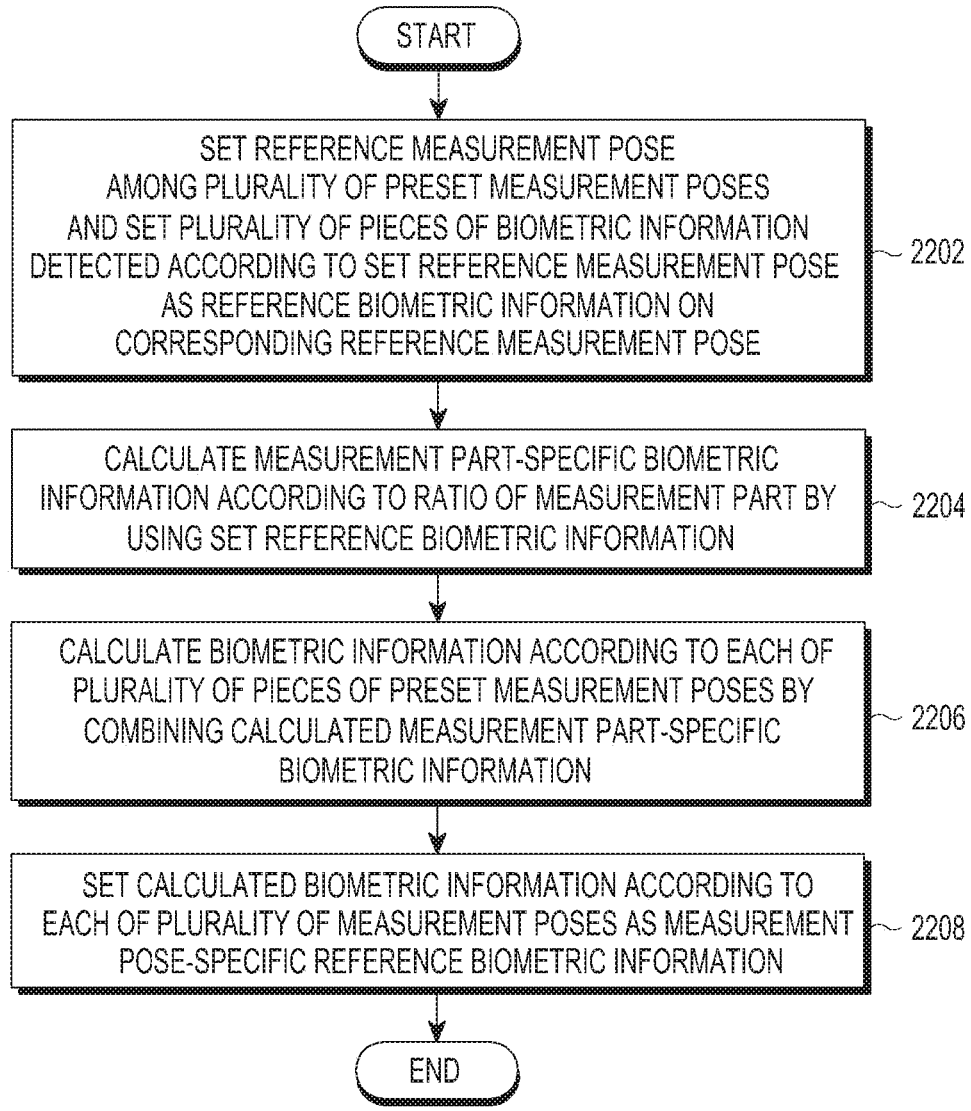
FIG. 22 is a flowchart illustrating a method of setting measurement pose-specific reference biometric information according to various embodiments of the present disclosure.

FIG. 22 is a flowchart illustrating a method of setting measurement pose-specific reference biometric information according to various embodiments of the present disclosure.

Referring to FIG. 22, the controller 1290 may set a reference measurement pose among a plurality of preset measurement poses and set a plurality of pieces of biometric information detected according to the set reference measurement pose as reference biometric information of the corresponding reference measurement pose in operation 2202. For example, the controller 1290 may set a first measurement pose as the reference measurement pose, and detect biometric information of the examinee from the biometric information measurement unit 1230 connected through a plurality of electrodes having a preset electrode array (see FIG. 16B) according to the first measurement pose and set the detected biometric information as reference biometric information on the first measurement pose.

In operation 2204, the controller 1290 may calculate measurement part-specific biometric information according to a ratio of the preset measurement part by using the set reference biometric information. For example, since the detected reference biometric information corresponds to impedance of RA-TR-RL, the controller 1290 may calculate each impedance of the arm, TR, and leg by using the detected impedance according to body fat percentages of the arm, TR, and leg. It is assumed that the left and RAs have the same value and the left and RLs have the same value. For example, when the detected reference biometric information, that is, a reference impedance value is 510Ω and impedance ratios according to preset body fat percentages of the arm, TR, and leg are 30:1:20, reference impedance of the arm may be calculated as about 300Ω, reference impedance of the TR may be calculated as about 10Ω, and reference impedance of the leg may be calculated as about 200Ω.

The controller 1290 may calculate biometric information (for example, impedance) according to each of the plurality of preset measurement poses by combining the pieces of calculated biometric information according to each measurement part in operation 2206. For example, in a case of the first measurement pose, the impedance detected in operation 2202 may be reference impedance of the first measurement pose. Since the third measurement pose corresponds to the LA-RA in a state where the user stretches the arms, an impedance value corresponding to the third measurement pose may be calculated using the calculated arm reference impedance. Since the second measurement pose corresponds to the LA-RA in a state where the user bends the arms, an impedance value corresponding to the second measurement pose may be calculated using the calculated arm reference impedance and a proximity value according to a degree of the bent arms. Since the fourth measurement pose corresponds to the LA-RA in a state where the user pinches a plurality of electrodes with fingers, an impedance value corresponding to the fourth measurement pose may be calculated using the calculated arm reference impedance and a strain gage value according to a degree of pressing corresponding electrodes with fingers.

The controller 1290 may set the plurality of pieces of calculated measurement pose-specific biometric information as measurement pose-specific reference biometric information in operation 2208. For example, the controller 1290 may set each of the impedance values corresponding to the first to fourth measurement poses calculated in operation 2206 as a reference impedance value of each measurement pose.

The measurement pose-specific reference biometric information set as described above may correct the measurement pose determined in operation 2108 of FIG. 21. Through the measurement pose correction, it is possible to more precisely determine the measurement pose and detect biometric information of the examinee. Accordingly, the user can detect accurate biometric information in various measurement poses.

According to an embodiment of the present disclosure, a method of measuring biometric information by an electronic device may include a process of detecting a plurality of pieces of location information, a plurality of pieces of biometric information, and a plurality of pieces of auxiliary detection information in a measurement point, a process of determining a measurement pose of an examinee according to an attitude of the electronic device in the measurement point based on the plurality of pieces of detected location information, the plurality of pieces of detected biometric information, and the plurality of pieces of detected auxiliary detection information, a process of controlling a switch unit including a plurality of switches corresponding to a plurality of electrodes, respectively, such that an electrode array of the plurality of electrodes formed on at least one surface of the electronic device corresponds to a preset electrode array corresponding to the determined measurement pose among preset measurement pose-specific electrode arrays and is connected to a biometric information measurement unit, and a process of analyzing health state information of the examinee based on the biometric information detected by the biometric information measurement unit through the plurality of electrodes.

According to an embodiment of the present disclosure, the process of determining the measurement pose of the examinee may include a process of calculating a direction and an angle of each axis changed from a reference direction and a reference angle of each axis of the complex location sensor unit by using the detected acceleration value and geomagnetic value, a process of recognizing a location and an attitude of the electronic device from the calculated direction and angle of each axis and the detected altitude value, a process of selecting a measurement pose corresponding to the recognized location and attitude of the electronic device, and the detected impedance value, skin conductivity value, strain gage value, proximity value, and temperature value within a preset measurement pose-specific location and attitude range of the electronic device, an impedance range, a skin conductivity range, a strain gage range, a proximity range, and a temperature range, and a process of determining the selected measurement pose as the measurement pose of the examinee.

According to an embodiment of the present disclosure, the process of controlling the switch unit may switch a corresponding switch of each electrode to change the array of the plurality of electrodes into an electrode array corresponding to the determined measurement pose among the preset measurement pose-specific electrode arrays.

According to an embodiment of the present disclosure, the electrode array may include an arrangement of current electrode channels for applying the current to different measurement parts according to the measurement pose and voltage electrode channels for detecting the voltage from the corresponding measurement part.

According to an embodiment of the present disclosure, the method of measuring the biometric information by the electronic device may further include a process of analyzing health state information of the examinee based on biometric information detected by the biometric information measurement unit through the plurality of electrodes.

According to an embodiment of the present disclosure, the process of analyzing the health state information of the examinee may analyze a body composition of the examinee based on body resistance detected by the biometric information measurement unit through the plurality of electrodes of the controlled electrode array corresponding to the determined measurement pose among the preset measurement pose-specific electrode arrays.

According to an embodiment of the present disclosure, the method of measuring the biometric information by the electronic device may further include a process of correcting the determined measurement pose in accordance with a biometric information difference between the biometric information detected through the plurality of electrodes and preset measurement pose-specific reference biometric information.

According to an embodiment of the present disclosure, the process of analyzing the health state information of the examinee may analyze a body composition of the examinee based on body resistance re-detected by the biometric information measurement unit through the plurality of electrodes of the controlled electrode array corresponding to the corrected measurement pose among the preset measurement pose-specific electrode arrays.

Figure 23A:
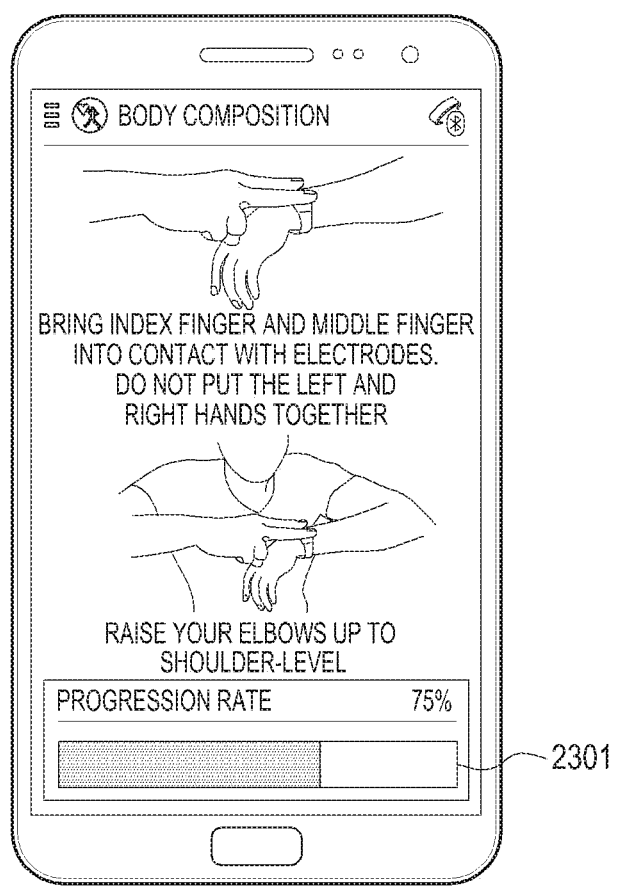
FIG. 23A illustrates a display screen showing a method of measuring a preset measurement pose when biometric information is measured according to various embodiments of the present disclosure.
Figure 23B:
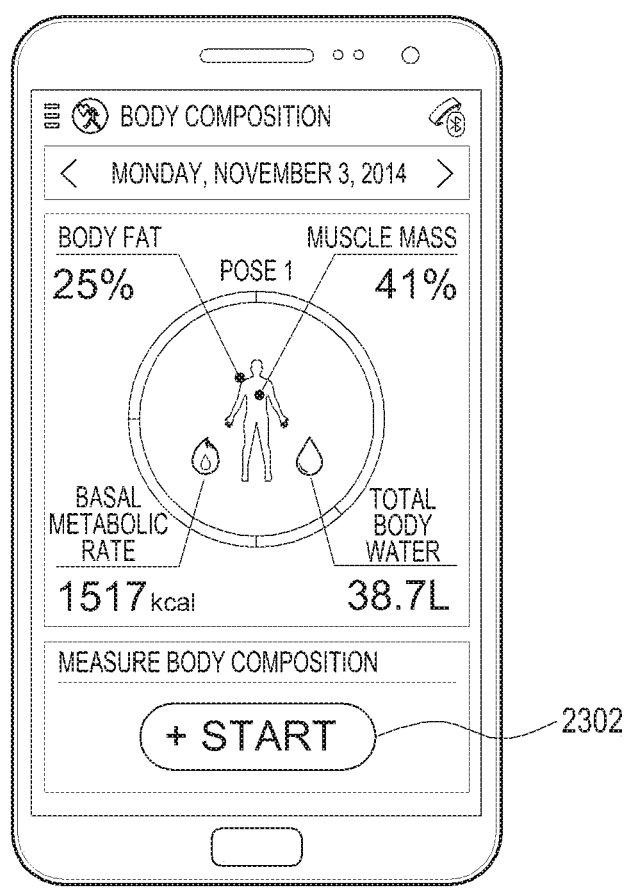
FIG. 23B illustrates a display screen showing a biometric information analysis result of a measurement pose according to various embodiments of the present disclosure.

FIG. 23A illustrates a display screen showing a method of measuring a preset measurement pose when biometric information is measured according to various embodiments of the present disclosure, and FIG. 23B illustrates a display screen showing a biometric information analysis result of a measurement pose according to various embodiments of the present disclosure.

Referring to FIG. 23A, the method of measuring the preset measurement pose is illustrated. For example, the measurement pose illustrated in FIG. 23A may correspond to the second measurement pose in which a body composition of the examinee can be measured through the LA-TR-RA. In the second measurement pose, if it is assumed that the most accurate body composition can be analyzed when elbows of both arms are flush with the shoulder, the controller 1290 may display a screen for guiding the second measurement pose on the screen of the display unit 1270. For example, an action which the examinee should take and matters which the examinee should attend to may be displayed through graphics and a notification statement (for example, "Bring an index finger and a middle finger into contact with the electrode. Do not put the left and right hands together" and "Raise your elbows up to shoulder-level") on the screen of the display unit 1270. Further, a measurement process rate display area 2301 for displaying a measurement progress rate after the measurement starts may be further displayed on the screen.

Referring to FIG. 23B, the controller 1290 may display a body composition analysis result according to an automatically recognized measurement pose of the examinee on the screen of the display unit 1270. The measurement pose (for example, measurement 2), an amount of body fat (%), muscle mass (%), a basal metabolic rate (Kcal), and total body water (L) may be displayed on the screen. In addition, not illustrated in FIG. 23B, various body composition analysis results including balance of right and left, balance of top and bottom, a BMI, and an abdominal obesity level may be variously displayed in a text form or a graphic form, such as a graph or a diagram. A measurement start button 2302 for starting the body composition measurement may be further displayed on the screen. By pressing the measurement start button 2302, it is possible to start body composition measurement of another examinee or start the body composition measurement of the same examinee and to date the body composition analysis result.

Figure 24:
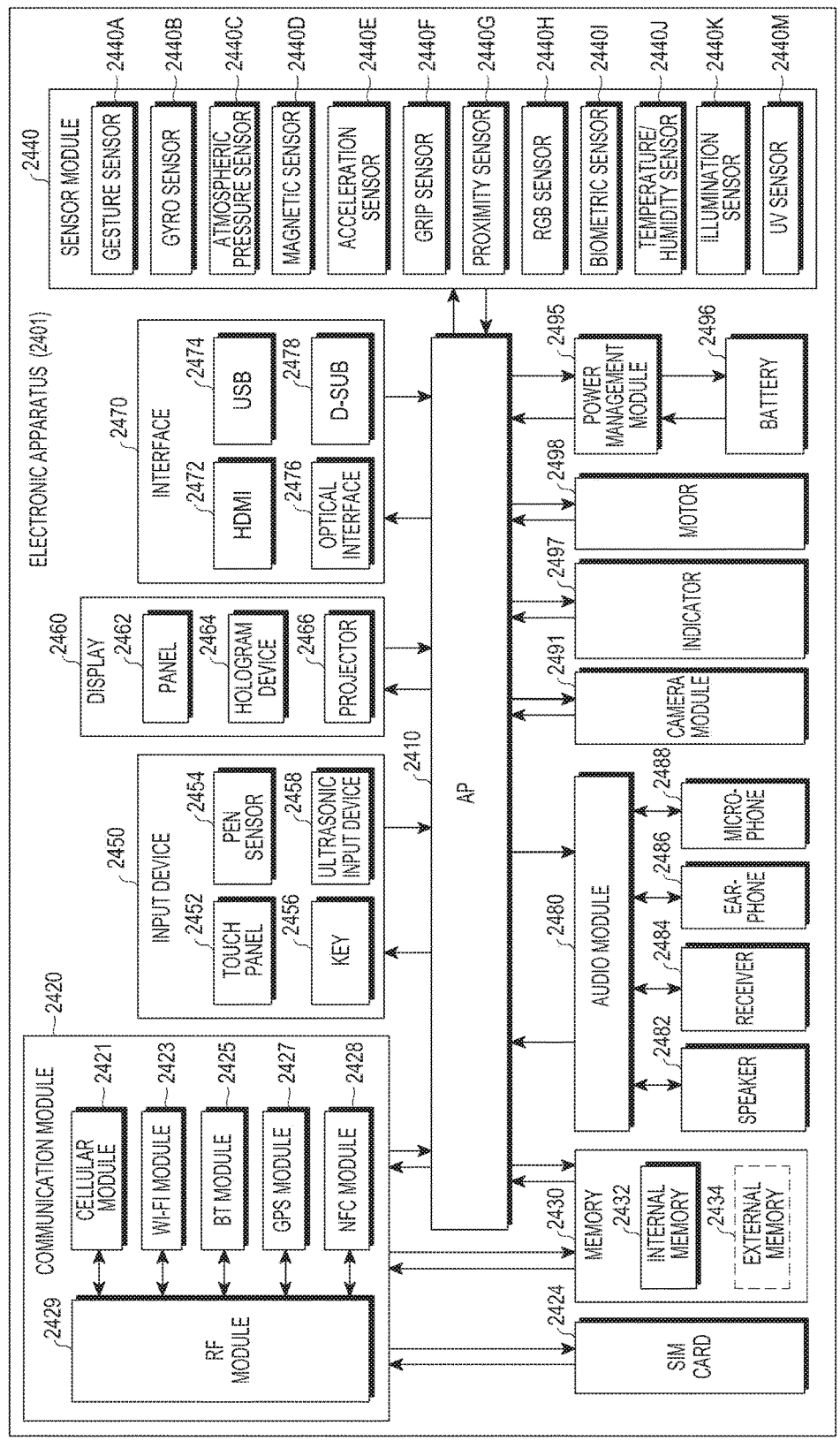
FIG. 24 is a block diagram of an electronic device according to various embodiments.

FIG. 24 is a block diagram of an electronic device according to various embodiments of the present disclosure.

Referring to FIG. 24, an electronic device 2401 may include, for example, all or a part of the electronic device 101 illustrated in FIG. 1. The electronic device 2401 may include at least one AP 2410, a communication module 2420, a subscriber identification module (SIM) card 2424, a memory 2430, a sensor module 2440, an input device 2450, a display 2460, an interface 2470, an audio module 2480, a camera module 2491, a power management module 2495, a battery 2496, an indicator 2497, and a motor 2498.

The AP 2410 may control a plurality of hardware or software components connected thereto by driving an OS or an application program and perform a variety of data processing and calculations. The AP 2410 may be implemented by, for example, a system on chip (SoC). According to an embodiment of the present disclosure, the AP 2410 may further include a graphics processing unit (GPU) and/or an image signal processor (ISP). The AP 2410 may include at least some of the elements (for example, a cellular module 2421) illustrated in FIG. 24. The AP 2410 may load commands or data, received from at least one other element (for example, a non-volatile memory), in a volatile memory to process the loaded commands or data, and may store various types of data in the non-volatile memory.

The communication module 2420 may have a configuration that is the same as or similar to that of the communication interface 170 of FIG. 1. The communication module 2420 may include, for example, the cellular module 2421, a Wi-Fi module 2423, a Bluetooth (BT) module 2425, a GPS module 2427, a near field communication (NFC) module 2428, and a radio frequency (RF) module 2429.

The cellular module 2421 may provide, for example, a voice call, a video call, a text message service, or an Internet service through a communication network. According to an embodiment of the present disclosure, the cellular module 2421 may distinguish and authenticate the electronic device 201 in a communication network using a SIM (for example, the SIM card 2424). According to an embodiment of the present disclosure, the cellular module 2421 may perform at least some functions which the AP 2410 may provide. According to an embodiment of the present disclosure, the cellular module 2421 may include a CP.

The Wi-Fi module 2423, the BT module 2425, the GPS module 2427, or the NFC module 2428 may include, for example, a processor for processing data transmitted/received through the corresponding module. According to various embodiments of the present disclosure, at least some (for example, two or more) of the cellular module 2421, the Wi-Fi module 2423, the BT module 2425, the GPS module 2427, and the NFC module 2428 may be included in one integrated chip (IC) or IC package.

The RF module 2429 may transmit/receive, for example, a communication signal (for example, an RF signal). The RF module 2429 may include, for example, a transceiver, a power amp module (PAM), a frequency filter, a low noise amplifier (LNA), or an antenna. According to another embodiment of the present disclosure, at least one of the cellular module 2421, the Wi-Fi module 2423, the BT module 2425, the GPS module 2427, and the NFC module 2428 may transmit and receive RF signals through a separate RF module.

The SIM card 2424 may include, for example, a card including a SIM and/or an embedded SIM, and may further include unique identification information (for example, an integrated circuit card identifier (ICCID)) or subscriber information (for example, international mobile subscriber identity (IMSI)).

The memory 2430 (for example, the memory 130) may include, for example, an internal memory 2432 or an external memory 2432. The internal memory 2432 may include, for example, at least one of a volatile memory (for example, a dynamic random access memory (DRAM), a static RAM (SRAM), a synchronous dynamic RAM (SDRAM), and the like) and a non-volatile memory (for example, a one-time programmable read only memory (OTPROM), a programmable ROM (PROM), an erasable and programmable ROM (EPROM), an electrically erasable and programmable ROM (EEPROM), a mask ROM, a flash ROM, a flash memory (for example, a NAND flash memory or a NOR flash memory), a hard disc drive, a solid state drive (SSD), and the like).

The external memory 2434 may further include a flash drive, for example, a compact flash (CF), a secure digital (SD), a micro-SD, a mini-SD, an extreme digital (xD), a memory stick, and the like. The external memory 2434 may be functionally and/or physically connected to the electronic device 2401 through various interfaces.

The sensor module 2440 may, for example, measure a physical quantity or detect an operating state of the electronic device 2401, and may convert the measured or detected information into an electrical signal. The sensor module 2440 may include, for example, at least one of, a gesture sensor 2440A, a gyro sensor 2440B, an atmospheric pressure sensor 2440C, a magnetic sensor 2440D, an acceleration sensor 2440E, a grip sensor 2440F, a proximity sensor 2440G, a color sensor 2440H (for example, red, green, and blue (RGB) sensor), a bio-sensor 2440I, a temperature/humidity sensor 2440J, an illumination sensor 2440K, and a ultra violet (UV) sensor 2440M. Additionally or alternatively, the sensor module 2440 may include an E-nose sensor, an EMG sensor, an EEG sensor, an ECG sensor, an infrared (IR) sensor, an iris sensor, and/or a fingerprint sensor. The sensor module 2440 may further include a control circuit for controlling one or more sensors included therein. In an embodiment of the present disclosure, the electronic device 2401 may further include a processor configured to control the sensor module 2440 as a part of or separately from the AP 2410, and may control the sensor module 2440 while the AP 2410 is in a sleep mode.

The input device 2450 may include, for example, a touch panel 2452, a (digital) pen sensor 2454, a key 2456, or an ultrasonic input device 2458. The touch panel 2452 may use at least one of, for example, a capacitive type, a resistive type, an infrared type, and an ultrasonic type. In addition, the touch panel 2452 may further include a control circuit. The touch panel 2452 may further include a tactile layer to provide a tactile reaction to a user.

The (digital) pen sensor 2454 may be, for example, a part of the touch panel, or may include a separate recognition sheet. The key 2456 may include, for example, a physical button, an optical key, or a keypad. The ultrasonic input device 2458 may identify data by detecting acoustic waves with a microphone (for example, a microphone 2488) of the electronic device 2401 through an input unit for generating an ultrasonic signal.

The display 2460 (for example, the display 160) may include a panel 2462, a hologram device 2464, or a projector 2466. The panel 2462 may include a configuration that is the same as or similar to that of the display 160 of FIG. 1. The panel 2462 may be implemented to be, for example, flexible, transparent, or wearable. The panel 2462 may be configured as a single module integrated with the touch panel 2452. The hologram device 2464 may show a stereoscopic image in the air using interference of light. The projector 2466 may project light onto a screen to display an image. The screen may be located, for example, in the interior of or on the exterior of the electronic device 2401. According to an embodiment of the present disclosure, the display 2460 may further include a control circuit for controlling the panel 2462, the hologram device 2464, or the projector 2466.

The interface 2470 may include, for example, an HDMI 2472, a USB 2474, an optical interface 2476, or a D-sub-miniature (D-sub) 2478. The interface 2470 may be included in, for example, the communication interface 170 illustrated in FIG. 1. Additionally or alternatively, the interface 2470 may include, for example, a mobile high-definition link (MHL) interface, an SD card/multi-media card (MMC) interface, or an infrared data association (IrDA) standard interface.

The audio module 2480 may convert, for example, a sound into an electrical signal, and vice versa. At least some elements of the audio module 2480 may be included in, for example, the input/output interface 150 illustrated in FIG. 1. The audio module 2480 may, for example, process sound information that is input or output through a speaker 2482, a receiver 2484, earphones 2486, the microphone 2488, and the like.

The camera module 2491 may take a still image and a moving image. According to an embodiment of the present disclosure, the camera module 291 may include one or more image sensors (for example, a front sensor and a rear sensor), a lens, an ISP, or a flash (for example, an LED or a xenon lamp).

The power management module 2495 may manage, for example, power of the electronic device 2401. According to an embodiment of the present disclosure, the power management module 2495 may include a power management integrated circuit (PMIC), a charger IC, or a battery or fuel gauge. The PMIC may have a wired and/or wireless charging scheme. Examples of the wireless charging method may include, for example, a magnetic resonance method, a magnetic induction method, an electromagnetic method, and the like. Additional circuits (for example, a coil loop, a resonance circuit, a rectifier, and the like) for wireless charging may be further included. The battery gauge may measure, for example, a residual quantity of the battery 2496, and a voltage, a current, or a temperature while charging. The battery 2496 may include, for example, a rechargeable battery and/or a solar battery.

The indicator 2497 may indicate a specific state of the electronic device 2401 or a part thereof (for example, the AP 2410), for example, a booting state, a message state, a charging state, and the like. The motor 2498 may convert an electrical signal into a mechanical vibration, and may generate a vibration or haptic effect. Although not illustrated, the electronic device 2401 may include a processing unit (for example, a GPU) for mobile TV support. The processing device for mobile TV support may process, for example, media data according to a standard of digital multimedia broadcasting (DMB), digital video broadcasting (DVB), media flow, and the like.

Each of the components of the electronic device according to the present disclosure may be implemented by one or more components and the name of the corresponding component may vary depending on a type of the electronic device. In various embodiments of the present disclosure, the electronic device may include at least one of the above-described elements. Some of the above-described elements may be omitted from the electronic device, or the electronic device may further include additional elements. Further, some of the components of the electronic device according to the various embodiments of the present disclosure may be combined to form a single entity, and thus, may equivalently execute functions of the corresponding elements prior to the combination.

Figure 25:
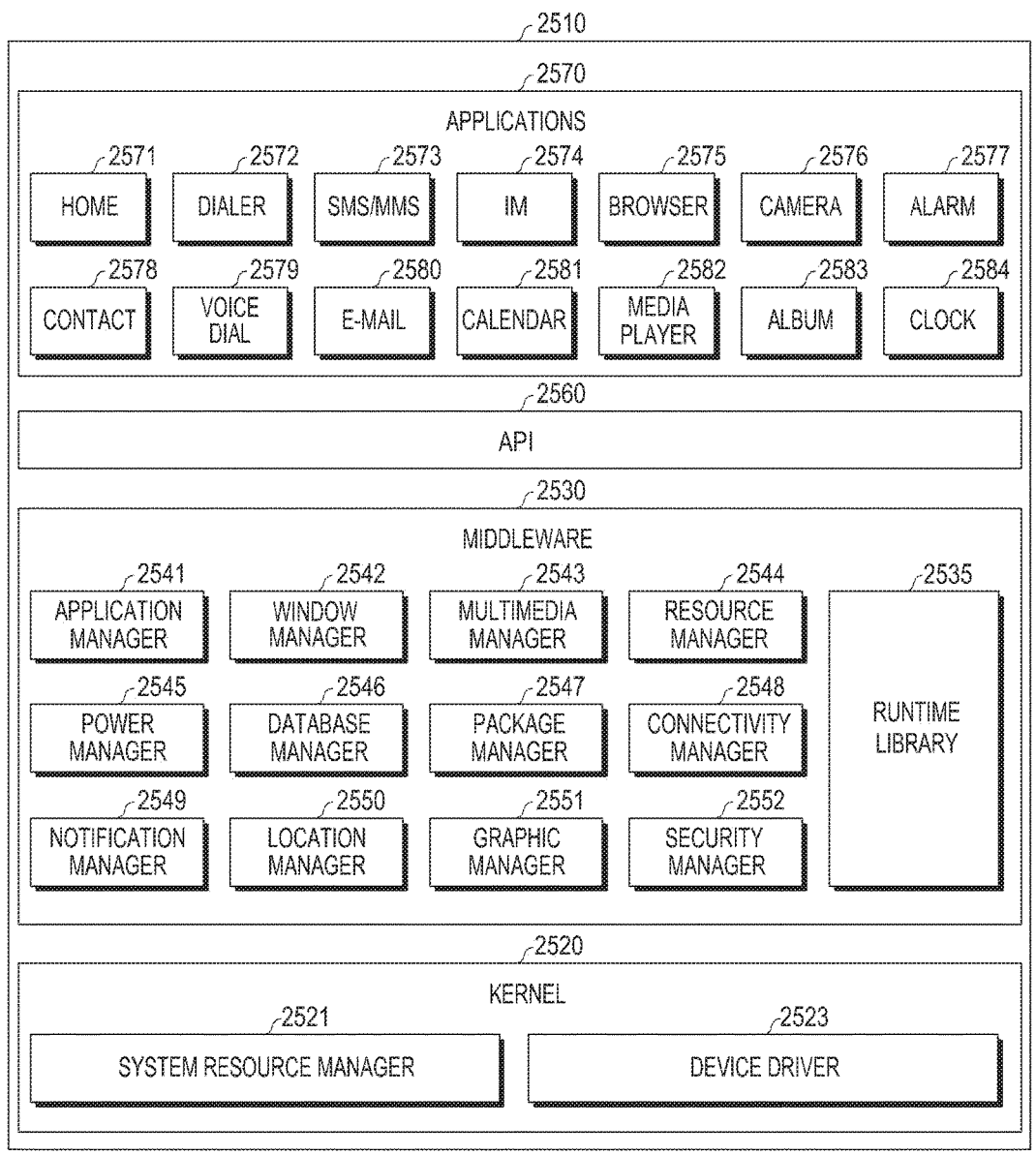
FIG. 25 is a block diagram of a program module according to various embodiments.

FIG. 25 is a block diagram of a program module according to various embodiments of the present disclosure.

Referring to FIG. 25, according to an embodiment of the present disclosure, a program module 2510 (for example, the program 140) may include an OS for controlling resources related to an electronic device (for example, the electronic device 101) and/or various applications (for example, the application programs 147) executed in the OS. The OS may be, for example, Android, iOS, Windows, Symbian, Tizen, Bada, and the like.

The programming module 2510 may include a kernel 2520, middleware 2530, an API 2560, and/or applications 2570. At least some of the program module 2510 may be preloaded in the electronic device, or may be downloaded from a server (for example, the server 106).

The kernel 2520 (for example, the kernel 141 of FIG. 1) may include, for example, a system resource manager 2521 or a device driver 2523. The system resource manager 2521 may control, allocate, or collect system resources. According to an embodiment of the present disclosure, the system resource manager 2521 may include a process management unit, a memory management unit, a file system management unit, and the like. The device driver 2523 may include, for example, a display driver, a camera driver, a BT driver, a shared-memory driver, a USB driver, a keypad driver, a Wi-Fi driver, an audio driver, or an inter-process communication (IPC) driver.

The middleware 2530 may provide a function required by the applications 2570 in common or provide various functions to the applications 2570 through the API 2560 so that the applications 2560 may efficiently use limited system resources of the electronic device. According to an embodiment of the present disclosure, the middleware 2530 (for example, the middleware 143) may include at least one of a run time library 2535, an application manager 2541, a window manager 2542, a multimedia manager 2543, a resource manager 2544, a power manager 2545, a database manager 2546, a package manager 2547, a connectivity manager 2548, a notification manager 2549, a location manager 2550, a graphic manager 2551, and a security manager 2552.

The runtime library 2535 may include, for example, a library module used by a complier in order to add a new function through a programming language during the execution of the applications 2570. The runtime library 2535 may perform input/output management, memory management, or a function for an arithmetic function.

The application manager 2541 may manage, for example, a life cycle of at least one of the applications 2570. The window manager 2542 may manage a graphical user interface (GUI) resource used on a screen. The multimedia manager 2543 may identify a format required for reproducing various media files, and may encode or decode a media file using a codec suitable for the corresponding format. The resource manager 2544 may manage resources of at least one of the applications 2570, such as a source code, a memory, a storage space, and the like.

The power manager 2545 may operate together with, for example, a basic input/output system (BIOS) to manage a battery or power and provide power information required for an operation of the electronic device. The database manager 2546 may generate, search, or change a database to be used by at least one of the applications 2570. The package manager 2547 may manage installation or update of an application distributed in the format of a package file.

The connectivity manager 2548 may manage, for example, a wireless connection, such as Wi-Fi or BT. The notification manager 2549 may display or notify of an event, such as a received message, an appointment, and a proximity notification, in such a manner as not to disturb a user. The location manager 2550 may manage location information of the electronic device. The graphic manager 2551 may manage a graphic effect to be provided to a user, or a user interface related thereto. The security manager 2552 may provide all security functions required for system security or user authentication. According to an embodiment of the present disclosure, when the electronic device (for example, the electronic device 101) has a call function, the middleware 2530 may further include a telephony manager for managing a voice call function or a video call function of the electronic device.

The middleware 2530 may include a middleware module that forms a combination of various functions of the aforementioned elements. The middleware 2530 may provide specialized modules according to the types of OSs in order to provide differentiated functions. In addition, the middleware 2530 may dynamically remove some of the existing elements, or may add new elements.

The API 2560 (for example, the API 145) may be, for example, a set of API programming functions, and may be provided with different configurations according to OSs. For example, in the case of Android or iOS, one API set may be provided for each platform, and in the case of Tizen, two or more API sets may be provided for each platform.

The applications 2570 (for example, the application programs 147) may include, for example, one or more applications that can provide functions, such as a home application 2571, a dialer application 2572, a short message system (SMS)/multimedia message system (MIMS) application 2573, an instant message (IM) application 2574, a browser application 2575, a camera application 2576, an alarm application 2577, a contact application 2578, a voice dial application 2579, an e-mail application 2580, a calendar application 2581, a media player application 2582, an album application 2583, a clock application 2584, health care application (for example, to measure exercise quantity or blood sugar), or environment information application (for example, atmospheric pressure, humidity, or temperature information).

According to an embodiment of the present disclosure, the applications 2570 may include an application (hereinafter, referred to as an "information exchange application" for convenience of the description) that supports information exchange between the electronic device (for example, the electronic device 101) and external electronic devices (for example, the first external electronic device 102 and the second external electronic device 104). The information exchange application may include, for example, a notification relay application for transmitting specific information to the external electronic device, or a device management application for managing the external electronic device.

For example, the notification relay application may include a function of transferring, to an external electronic device (for example, the first external electronic device 102 or the second external electronic device 104), notification information generated from other applications of the electronic device (for example, an SMS/MMS application, an e-mail application, a health management application, or an environmental information application). Furthermore, the notification relay application may, for example, receive notification information from an external electronic device and provide the received notification information to a user. The device management application may, for example, manage (for example, install, delete, or update) at least one function of an external electronic device (for example, the second external electronic device 104) communicating with the electronic device (for example, a function of turning on/off the external electronic device itself (or some elements thereof), or a function of adjusting luminance (or a resolution) of the display), applications operating in the external electronic device, or services provided by the external electronic device (for example, a telephone call service or a message service).

According to an embodiment of the present disclosure, the applications 2570 may include an application (for example, health management application) designated according to attributes (for example, attributes of the electronic device, such as the type of electronic device which corresponds to a mobile medical device) of the external electronic device (for example, the first external electronic device 102 or the second external electronic device 104). According to an embodiment of the present disclosure, the applications 2570 may include an application received from the external electronic device (for example, the server 106, or the first external electronic device 102, or the second external electronic device 104). According to an embodiment of the present disclosure, the applications 2570 may include a preloaded application or a third party application that can be downloaded from a server. Names of the elements of the program module 1710, according to the above-described embodiments of the present disclosure, may change depending on the type of OS.

According to various embodiments of the present disclosure, at least some of the program module 2510 may be implemented in software, firmware, hardware, or a combination of two or more thereof. At least some of the programming module 2510 may be implemented (for example, executed) by, for example, the processor (for example, the AP 2410). At least some of the programming module 2510 may include, for example, a module, a program, a routine, sets of instructions, a process, and the like, for performing one or more functions.

The term "module" as used herein may, for example, mean a unit including one of hardware, software, and firmware or a combination of two or more of them. The "module" may be interchangeably used with, for example, the term "unit", "logic", "logical block", "component", or "circuit". The module may be a minimum unit of an integrated component element or a part thereof. The "module" may be the smallest unit configured to perform one or more functions or a part thereof. The module may be mechanically or electronically implemented. For example, the "module" according to the present disclosure may include at least one of an application-specific integrated circuit (ASIC) chip, a field-programmable gate arrays (FPGA), and a programmable-logic device for performing operations which has been known or are to be developed hereinafter.

According to various embodiments of the present disclosure, at least some of the devices (for example, modules or functions thereof) or the method (for example, operations) according to the present disclosure may be implemented by a command stored in a computer-readable storage medium in a programming module form. The instruction, when executed by a processor (for example, the processor 120), may cause the one or more processors to execute the function corresponding to the instruction. The computer-readable storage medium may be, for example, the memory 130.

Certain aspects of the present disclosure can also be embodied as computer readable code on a non-transitory computer readable recording medium. A non-transitory computer readable recording medium is any data storage device that can store data which can be thereafter read by a computer system. Examples of the non-transitory computer readable recording medium include a Read-Only Memory (ROM), a Random-Access Memory (RAM), Compact Disc-ROMs (CD-ROMs), magnetic tapes, floppy disks, and optical data storage devices. The non-transitory computer readable recording medium can also be distributed over network coupled computer systems so that the computer readable code is stored and executed in a distributed fashion. In addition, functional programs, code, and code segments for accomplishing the present disclosure can be easily construed by programmers skilled in the art to which the present disclosure pertains.

At this point it should be noted that the various embodiments of the present disclosure as described above typically involve the processing of input data and the generation of output data to some extent. This input data processing and output data generation may be implemented in hardware or software in combination with hardware. For example, specific electronic components may be employed in a mobile device or similar or related circuitry for implementing the functions associated with the various embodiments of the present disclosure as described above. Alternatively, one or more processors operating in accordance with stored instructions may implement the functions associated with the various embodiments of the present disclosure as described above. If such is the case, it is within the scope of the present disclosure that such instructions may be stored on one or more non-transitory processor readable mediums. Examples of the processor readable mediums include a ROM, a RAM, CD-ROMs, magnetic tapes, floppy disks, and optical data storage devices. The processor readable mediums can also be distributed over network coupled computer systems so that the instructions are stored and executed in a distributed fashion. In addition, functional computer programs, instructions, and instruction segments for accomplishing the present disclosure can be easily construed by programmers skilled in the art to which the present disclosure pertains.

The programming module according to the present disclosure may include one or more of the aforementioned components or may further include other additional components, or some of the aforementioned components may be omitted. Operations executed by a module, a programming module, or other component elements according to various embodiments of the present disclosure may be executed sequentially, in parallel, repeatedly, or in a heuristic manner. Further, some operations may be executed according to another order or may be omitted, or other operations may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device for measuring biometric information, the electronic device comprising:
    a plurality of sensors configured to detect an attitude of the electronic device;
    a biometric information measurement detector configured to detect biometric information on an examinee through a plurality of electrodes formed on at least one surface of the electronic device;
    a plurality of switches electrically connected to the plurality of electrodes; and
    at least one processor configured to:
        recognize an array of the plurality of electrodes based on the detected attitude of the electronic device, and
        control the plurality of switches such that the recognized electrode array corresponds to a preset electrode array.

2. The electronic device of claim 1, wherein the plurality of sensors comprises:
    an acceleration sensor configured to detect an acceleration value of the electronic device according to a movement to a measurement point;
    a geomagnetic sensor configured to detect a geomagnetic value of the electronic device at the measurement point; and
    an altitude sensor configured to detect an altitude value of the electronic device at the measurement point.

3. The electronic device of claim 2, wherein the biometric information measurement detector comprises a biometric signal measurement device configured to detect a biometric signal of the examinee.

4. The electronic device of claim 3, wherein the biometric signal measurement device detects one of an electrocardiography (ECG) signal, an electroencephalogram (EEG) signal, an electrooculogram (EOG) signal, an electrogastrogram (EGG) signal, or an electromyography (EMG) signal.

5. The electronic device of claim 3, wherein the at least one processor comprises:
    a measurement location recognition device configured to recognize a location and the attitude of the electronic device at the measurement point by using at least one of the detected acceleratation value, geomagnetic value or altitude value;
    an electrode array determination device configured to:
        recognize the array of the plurality of electrodes according to the recognized location and attitude of the electronic device,
        compare the recognized electrode array and the preset electrode array, and
        determine whether the electrode array is changed; and
    a switch control device configured to control the plurality of switches such that the recognized electrode array corresponds to the preset electrode array and is connected to the biometric information measurement detector according to a result of the determination.

6. The electronic device of claim 5, wherein the measurement location recognition device is further configured to:
    calculate a direction and an angle of each axis changed from a reference direction and a reference angle of each axis of the plurality of sensors by using the detected acceleration value and geomagnetic value, and
    recognize the location and the attitude of the electronic device based on the calculated direction and angle of each axis and the detected altitude value.

7. The electronic device of claim 5, wherein the electrode array determination device is further configured to:
    compare whether the recognized electrode array of each electrode matches the preset electrode array of the corresponding electrode, and
    determine, when the recognized electrode array of at least one electrode is not equal to the preset electrode array of the corresponding electrode, that the recognized electrode array is changed.

8. The electronic device of claim 7, wherein, when the recognized electrode array is changed, the switch control device is further configured to switch a corresponding switch to connect the preset electrode array of the corresponding electrode changed from the changed electrode array of the corresponding electrode to the biometric information measurement detector.

9. The electronic device of claim 8, wherein the electrode array comprises a location, direction, polarity, arrangement of electrode channels of each electrode.

10. The electronic device of claim 5, wherein the at least one processor further comprises a biometric information analysis device configured to analyze health state information of the examinee by analyzing the biometric information detected through the controlled electrode array of the plurality of electrodes.

11. The electronic device of claim 10, wherein the biometric information analysis device is further configured to analyze a biometric index of the examinee based on the detected biometric signal.

12. The electronic device of claim 10, wherein the at least one processor further comprises a biometric information conversion device configured to convert, when the recognized electrode array is changed, the detected biometric signal to compensate for a difference between the recognized electrode array and the preset electrode array.

13. A method of measuring biometric information by an electronic device, the method comprising:
- detecting an attitude of the electronic device;
- recognizing an array of a plurality of electrodes formed on at least one surface of the electronic device based on the detected attitude;
- determining whether the recognized electrode array is changed by comparing the recognized electrode array and a preset electrode array; and
- controlling a plurality of switches corresponding to the plurality of electrodes, respectively, such that the recognized electrode array corresponds to the preset electrode array and is connected to a biometric information measurement unit based on a result of the determination.

14. The method of claim 13, wherein the recognizing of the array of the plurality of electrodes comprises:
- detecting an acceleration value, a geomagnetic value, and an altitude value of the electronic device in a measurement point by a sensor unit;
- calculating a direction and an angle of each axis changed from a reference direction and a reference angle of each axis of the sensor unit by using the detected acceleration value and geomagnetic value;
- recognizing a location and the attitude of the electronic device from the calculated direction and angle of each axis and the detected altitude value; and
- recognizing the array of the plurality of electrodes according to the recognized location and attitude of the electronic device.

15. The method of claim 13, wherein the determining of whether the recognized electrode array is changed comprises:
- comparing the recognized electrode array of each electrode with a preset electrode array of the corresponding electrode; and
- determining, when the recognized electrode array of at least one electrode is not equal to the preset electrode array of the corresponding electrode based on a result of the comparison, that the recognized electrode array is changed.

16. The method of claim 15, wherein the controlling of the switch unit comprises controlling, when the recognized electrode array is changed, a corresponding switch to switch the changed electrode array of the corresponding electrode into the preset electrode array of the corresponding electrode.

17. The method of claim 16, further comprising analyzing health state information of an examinee by detecting biometric information through the plurality of electrodes by the biometric information measurement unit.

18. The method of claim 17, wherein the analyzing of the health state information of the examinee comprises analyzing a biometric index of the examinee based on a biometric signal detected through the plurality of electrodes of the controlled electrode array by the biometric information measurement unit.

19. The method of claim 17, further comprising converting, when the recognized electrode array is changed, the detected biometric signal to compensate for a difference between the recognized electrode array and the preset electrode array.

20. The method of claim 19, wherein the analyzing of the health state information of the examinee comprises analyzing a biometric index of the examinee based on a biometric signal detected by the biometric information measurement unit through the plurality of electrodes of the recognized electrode array.

* * * * *